United States Patent
Zhi et al.

(10) Patent No.: US 12,237,051 B2
(45) Date of Patent: *Feb. 25, 2025

(54) METHODS AND SYSTEM FOR EFFICIENT INDEXING FOR GENETIC GENEALOGICAL DISCOVERY IN LARGE GENOTYPE DATABASES

(71) Applicants: University of Central Florida Research Foundation, Inc., Orlando, FL (US); The Board of Regents of the University of Texas System, Austin, TX (US)

(72) Inventors: Degui Zhi, Houston, TX (US); Shaojie Zhang, Orlando, FL (US); Ardalan Naseri, Houston, TX (US); Ahsan Sanaullah, Orlando, FL (US); Erwin Holzhauser, Orlando, FL (US)

(73) Assignees: University of Central Florida Research Foundation, Inc., Orlando, FL (US); The Board of Regents of the University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/505,757

(22) Filed: Nov. 9, 2023

(65) Prior Publication Data

US 2024/0087671 A1     Mar. 14, 2024

Related U.S. Application Data

(63) Continuation of application No. 16/840,145, filed on Apr. 3, 2020, now Pat. No. 11,848,073.
(Continued)

(51) Int. Cl.
*G16B 10/00*    (2019.01)
*G06F 16/22*    (2019.01)
(Continued)

(52) U.S. Cl.
CPC ............ *G16B 10/00* (2019.02); *G06F 16/22* (2019.01); *G06F 16/24* (2019.01); *G16B 20/20* (2019.02); *G16B 30/00* (2019.02)

(58) Field of Classification Search
None
See application file for complete search history.

(56) References Cited

U.S. PATENT DOCUMENTS

| 6,703,228 B1 * | 3/2004 | Landers ............... C12Q 1/686 536/24.31 |
| 9,904,763 B2 * | 2/2018 | Kural ................... G16B 50/00 |

(Continued)

OTHER PUBLICATIONS

Wei, Y. et al. Genetic and population analysis: RaPID-Query for fast identity by descent search and genealogical analysis. Bioinformatics, 2023, 39(6), btad312.
(Continued)

*Primary Examiner* — Farhan M Syed
(74) *Attorney, Agent, or Firm* — Austin Acebo; Anton J. Hopen; Smith & Hopen, P.A.

(57) ABSTRACT

A system for indexing, updating, and search haplotypes for genetic genealogical discovery in genotype databases. The system includes a pool of genetic indexes, a haplotype ingestion engine, and a haplotype query engine. The haplotypes of a number of individuals in a genotype database are indexed by a pool of multiple panels, and each panel pool can be dynamically updated by the insertion or deletion of individual haplotypes. A genetic genealogical search of a query haplotype against the database is achieved by first projecting the query onto a subset of panels in the pool, then conducting long match queries over each panel, and finally aggregating the identified long matches into Identical-by-Descent segments, i.e., DNA matches, between the query and the haplotypes in the database.

19 Claims, 21 Drawing Sheets
(17 of 21 Drawing Sheet(s) Filed in Color)

Related U.S. Application Data

(60) Provisional application No. 62/868,667, filed on Jun. 28, 2019, provisional application No. 62/828,894, filed on Apr. 3, 2019.

(51) Int. Cl.
*G06F 16/24* (2019.01)
*G16B 20/20* (2019.01)
*G16B 30/00* (2019.01)

(56) References Cited

U.S. PATENT DOCUMENTS

| | | | | |
|---|---|---|---|---|
| 10,053,736 B2 * | 8/2018 | Kural | .................. | G16B 30/10 |
| 10,078,724 B2 * | 9/2018 | Kural | .................. | G16B 30/20 |
| 10,192,026 B2 * | 1/2019 | Semenyuk | ............. | G16B 15/00 |
| 10,262,102 B2 * | 4/2019 | Brown | ................... | G16B 20/20 |
| 10,364,468 B2 * | 7/2019 | Lee | ........................ | G16B 30/00 |
| 10,724,110 B2 * | 7/2020 | Locke | ................... | G16B 30/00 |
| 10,790,044 B2 * | 9/2020 | Semenyuk | ............. | G16B 50/50 |
| 2002/0039990 A1 * | 4/2002 | Stanton, Jr. | .......... | C12Q 1/6883 |
| | | | | 435/6.16 |
| 2005/0191691 A1 * | 9/2005 | Stanton, Jr. | .......... | C12Q 1/6886 |
| | | | | 435/6.16 |
| 2014/0371110 A1 * | 12/2014 | Van Rooyen | ..... | H01L 21/76886 |
| | | | | 438/618 |
| 2020/0321073 A1 * | 10/2020 | Zhi | ........................ | G16B 30/00 |
| 2021/0020266 A1 * | 1/2021 | Freyman | ................ | G16B 50/30 |
| 2022/0154281 A1 * | 5/2022 | Boucher | ................ | G16B 40/20 |

OTHER PUBLICATIONS

Wang, V. et al. Sequence analysis: Syllable-PBWT for space-efficient haplotype long-match query. Bioinformatics, 39 (1), 2023, btac734.

* cited by examiner

| # Haplotypes | | 20k | 40k | 60k | 80k | 100k | 120k | 140k | 160k | 180k | 200k |
|---|---|---|---|---|---|---|---|---|---|---|---|
| Increasing Number of Matches | # Matches | 25359 | 50577 | 76110 | 101635 | 127167 | 152393 | 177852 | 203115 | 228499 | 253783 |
| | PBWT-Query (Memory-Extensive) | 0.381 | 1.054 | 1.739 | 2.554 | 2.348 | 2.783 | 2.847 | 3.393 | 3.577 | 6.022 |
| | L-PBWT-Query (Memory-Expansive) | 0.377 | 0.078 | 0.126 | 0.158 | 0.218 | 0.208 | 0.259 | 0.278 | 0.293 | 0.313 |
| | L-PBWT-Query (Memory-Mapped) | 0.394 | 0.390 | 0.556 | 0.501 | 0.462 | 0.611 | 0.597 | 0.602 | 0.741 | 0.678 |
| Same Number of Matches (253688) | Exhaustive Query Search | 0.854 | 1.651 | 2.362 | 6.868 | 10.038 | 12.773 | 15.363 | 19.986 | 22.584 | 26.685 |
| | PBWT-Query (Memory-Extensive) | 0.362 | 0.338 | 0.361 | 0.417 | 0.362 | 0.505 | 0.407 | 0.493 | 0.399 | 0.455 |
| | L-PBWT-Query (Memory-Extensive) | 0.014 | 0.048 | 0.066 | 0.083 | 0.076 | 0.116 | 0.083 | 0.113 | 0.140 | 0.137 |
| | L-PBWT-Query (Memory-Mapped) | 0.316 | 0.506 | 0.539 | 0.573 | 0.445 | 0.551 | 0.518 | 0.484 | 0.574 | 0.527 |

Fig. 6

| # Sites | | 20k | 40k | 60k | 80k | 100k | 120k | 140k | 160k | 180k | 200k |
|---|---|---|---|---|---|---|---|---|---|---|---|
| Increasing Number of Matches | # Matches | 69388 | 162130 | 274729 | 345291 | 423474 | 477398 | 548681 | 624393 | 728466 | 772025 |
| | PBWT-Query (Memory-Extensive) | 0.926 | 2.678 | 3.749 | 5.886 | 8.068 | 9.457 | 11.278 | 13.158 | 15.325 | 14.597 |
| | L-PBWT-Query (Memory-Extensive) | 0.085 | 0.139 | 0.234 | 0.372 | 0.653 | 0.692 | 0.882 | 1.23 | 1.383 | 1.501 |
| | L-PBWT-Query (Memory-Mapped) | 0.852 | 1.517 | 1.963 | 2.896 | 3.804 | 4.219 | 5.063 | 6.203 | 5.402 | 8.429 |
| Similar Number of Matches | # Matches | 69388 | 76770 | 76770 | 76770 | 76770 | 76770 | 76770 | 76770 | 76770 | 76770 |
| | PBWT-Query (Memory-Extensive) | 0.903 | 1.072 | 1.542 | 1.670 | 1.763 | 2.005 | 2.256 | 1.908 | 2.411 | 2.693 |
| | L-PBWT-Query (Memory-Extensive) | 0.095 | 0.163 | 0.121 | 0.172 | 0.264 | 0.412 | 0.407 | 0.633 | 0.654 | 0.853 |
| | L-PBWT-Query (Memory-Mapped) | 0.862 | 1.178 | 1.511 | 1.591 | 2.081 | 2.297 | 2.947 | 2.887 | 2.883 | 2.635 |

Fig. 8

| | PBWT-Query | L-PBWT-Query | L-PBWT-Query (memory-mapped) |
|---|---|---|---|
| Increasing # haplotypes (constant # matches) | 93.8 | 218.8 | 6.0 |
| Increasing # haplotypes (increasing # matches) | 93.8 | 218.8 | 6.0 |
| Increasing # sites (constant # matches) | 187.5 | 437.5 | 79.2 |
| Increasing # sites (increasing # matches) | 187.5 | 348.3 | 41.4 |

METHODS AND SYSTEM FOR EFFICIENT INDEXING FOR GENETIC GENEALOGICAL DISCOVERY IN LARGE GENOTYPE DATABASES

CROSS-REFERENCE TO RELATED APPLICATIONS

This nonprovisional application is a continuation of and claims priority to nonprovisional application Ser. No. 16/840,145, entitled "Methods and system for efficient indexing for genetic genealogical discovery in large genotype databases," filed Apr. 3, 2020, by the same inventors; which is a continuation of and claims priority to provisional application No. 62/828,894, entitled "Systems and method for fast, powerful, efficient and accurate genealogical searching, including haplotype matching between a query and a panel," filed Apr. 3, 2019, by the same inventors, and to provisional application No. 62/868,667, entitled "Systems and methods for ultra-fast, powerful, efficient and accurate detection of segments identical by descent in biobank-scale cohorts," filed Jun. 28, 2019, by the same inventors; the entireties of which are incorporated herein by reference.

FEDERALLY SPONSORED RESEARCH OR DEVELOPMENT

This invention was made with Government support under Grant No. R01HG010086 awarded by the US National Institutes of Health. The government has certain rights in the invention.

BACKGROUND OF THE INVENTION

1. Field of the Invention

This invention relates, generally, to population genetics. More specifically, it relates to improved genetic genealogical searching accomplished in an efficient and accurate manner by using a pool of PBWT (Positional Burrows-Wheeler Transform) genetic indexes, a haplotype ingestion engine, and a haplotype query engine.

2. Brief Description of the Prior Art

The increasing volumes of whole-genome genotype data, partly due to the steady drop in the cost of genotyping (Campbell et al., 2015; Jiang et al., 2016), offer a new opportunity to study genetic relationships and relatedness between individuals. In the public domain, biobank-scale SNP array projects have collected large amounts of genotype data. For example, UK Biobank has released genotype and health-related data of ~500 k individuals in the UK (Bycroft et al., 2018; Sudlow et al., 2015). However, this sample size is dwarfed by the collections in consumer genetics companies. As of July 2018, 23andMe® claims to have over 5 million customers and have collected the genotype data of all customers. AncestryDNA® has collected DNAs of more than 10 million individuals. It has been projected that genotype data of more than 100 million individuals will be available through direct-to-consumer companies by 2021 (Khan and Mittelman, 2018).

Genetic relationships among individuals are reflected in Identity by Descent (IBD) segments, shared DNA segments between a pair of individuals that have been inherited from a common ancestor. The length of IBD segments correlates with how recently two individuals share a common ancestor. A pair of individuals that share a common ancestor in a more recent generation may share more IBD segments, of larger length, compared with a pair of individuals that share a common ancestor less recently (Thompson, 2013). Therefore, in genotype or haplotype sequences, IBD segments that define a recent common ancestor correspond to long matches of DNA sequences. It has been projected that about 60% of individuals of European descent have a third-degree cousin or closer relative in a current database of over 1 million (Erlich et al., 2018) that can be found using IBD segments.

Previous research efforts were mostly focused on 'M-vs-M' matches of IBD segments. For a collection (panel) with M individuals or haplotypes, the goal was to identify all IBD segments between any pairs of individuals in the panel. Several methods have been proposed to detect all pairwise IBD segments in a panel (Browning and Browning, 2011, 2013a, b; Gusev et al., 2009; Purcell et al., 2007; Rodriguez et al., 2013, 2015). Most of these works rely on pairwise comparisons and thus with computational complexity $O(NM^2)$, where N is the length of the genome. GERMLINE (Gusev et al., 2009) is a fast 'M-vs-M' method claimed to be linear to the size of the panel [O(NM)] for random sequences. However, real genetic sequences typically contain repetitive local haplotypes and thus GERMLINE does not demonstrate linear behavior in real sequences. Durbin (2014) proposed an efficient genotype indexing method for storing and searching haplotype sequences.

For genealogical search, finding all matches greater than or equal to a certain length between a haplotype query and panel is desired. This can be thought of as finding all individuals in a panel related to the query that have a common ancestor in recent generations, which reveals more information about the query than set-maximal matches. A trivial example illustrates the point: in a large population containing a single pair of identical twins, the only set-maximal match that exists between any pair of individuals is the match between the twins spanning the length of the twins. All other relationships between any pair of individuals are missed. In the general case, to a lesser degree, examining only the longest set-maximal matches misses the majority of measurable genetic relationships between pairs of individuals in a population. The length of matches correlates with the number of generations that two individuals share a common ancestor. As a result, it can be applied to find multiple relatives of a given query individual up to a given degree of relatedness.

Accordingly, what is needed is an algorithm independent from the number of haplotypes for identifying all long IBD segments between a query and a panel, i.e. '1-vs-M' search, given M haplotypes in the panel. The time complexity being independent from the number of haplotypes or individuals is important because when the panel contains millions of individuals, naive methods of all pairwise comparison (with computational complexity O(NM)) will be too slow for real-time applications. However, no efficient on-line method yet exists to identify all long IBD segments between a query and a panel. GERMLINE (Gusev et al., 2009) does not yet offer a direct algorithm for '1-vs-M' search. Durbin's Algorithm 5 (Durbin, 2014) can find the single longest set-maximal matches between a query haplotype and all haplotypes in the panel with runtime O(N), i.e. independent from the number of haplotypes in the panel. However, in practice, multiple 'good enough' matches are desired for a genealogical search. Of note, one might be tempted to repeatedly apply Durbin's set-maximal matches algorithm and exclude the detected match at each run. This solution would not be practical, since the indices for the panel need to be re-computed or updated after each detected match. To date, there are no algorithms to find all L-long matches, matches longer than or equal to a given length L between a query and a panel of haplotypes, independent from M. There is also a need for an efficient, accurate, and cost-effective method that can power the needs of genetic genealogical discovery. Specifically, there is a need for a solution to allow efficient and real-time incremental updates of an existing large database. Accordingly, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an efficient, accurate, powerful, and cost-effective genetic genealogical discovery system that also supports dynamic updates, is now met by a new, useful, and nonobvious invention. In particular, the need for a system and method of efficient genealogical indexing that identifies all long IBD segments between a query and a panel, independent of the number of haplotypes, to identify ancestral relationships, is now met by the disclosed invention.

The novel method includes a step of providing a haplotype panel pool including a plurality of panels indexed by a positional Burrows-Wheeler transform (PBWT) representation, which may be dynamic. Each of the plurality of panels include a plurality of haplotypes, and the haplotype panel pool includes a set of variant sites which can be weighed to emphasize minor allele frequencies. Via a computing nodule in electronic communication with the haplotype panel pool, a minimum identity-by-descent segment length value is determined (and may be pre-determined). Haplotype matches greater than the minimum identity-by-descent segment length indicate a match between an input genetic sequence and the haplotype panel pool. Haplotype matches lesser than the minimum identity-by-descent segment length indicate a lack of a match between the input genetic sequence and the haplotype panel pool.

A plurality of portions of each of the plurality of panels is randomly selected to sample each of the plurality of panels. The sample is projected to the set of variant sites for each of the plurality of panels in the haplotype panel pool, such that the sample represents the haplotype panel pool and samples can be compared via the set of variants. The input genetic sequence is received at the computing nodule in electronic communication with the haplotype panel pool. An amount of the plurality of panels from the haplotype panel pool are activated for testing. The input genetic sequence is compared with the amount of the plurality of panels. Based on a determination that the input genetic sequence matches the amount of the plurality of panels by a value greater than the minimum identity-by-descent segment length, a genealogical match is determined between the input genetic sequence and the haplotype panel pool.

A long match query algorithm may be used to compare the input genetic sequence with the amount of the plurality of panels and determine if the input genetic sequence matches the amount of the plurality of panels by a value greater than the minimum identity-by-descent segment length. Moreover, the step of determining the minimum identity-by-descent segment length value can include a determination of at least one of a physical distance and a genetic distance between divergence value updates of a long match query algorithm.

The PBWT representation can be updated by adding or removing a haplotype. For example, a haplotype can be added into at least one or all of the plurality of panels by inserting the haplotype into a correct position at each variant site of the set of variants, and by calculating divergence values at positions forward from the inserted haplotype. In addition, a haplotype can be deleted from the haplotype panel pool by removing the haplotype from at least one or all of the plurality of panels.

An object of the invention is to improve the efficiencies related to genealogical indexing while simultaneously improving test accuracy by using a dynamic PBWT haplotype panel pool, a haplotype-ingestion engine, and a haplotype querying engine to compare a target haplotype against a dynamically-updated panel pool of haplotypes to identify all long matches above a certain length cutoff.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which:

FIG. 2 depicts an example of virtually inserting a new query haplotype to a PBWT panel at site k. The haplotype sequences of the panel are sorted based on the reversed prefix order in the PBWT panel at site k.

FIG. 4 depicts a haplotype panel with its corresponding indices to facilitate the search for L-long matches for L=4 ending at site 30, exclusive. The indices $I_{ps}^{30}$, $I_{pd}^{30}$, $I_{ns}^{30}$, and $I_{nd}^{30}$ allow jumping from any $y_i^{30}[30]$ to the nearest $y_j^{30}[30]$ preceding or proceedingy $y_i^{30}[30]$, such that $y_i^{30}[30] = y_j^{30}[30]$ or $y_i^{30}[30] \neq y_j^{30}[30]$. The indices $D_{ps}^{30}$, $D_{pd}^{30}$, $D_{ns}^{30}$, and $D_{nd}^{30}$ provide the largest divergence values from haplotypes skipped using $I_{ps}^{30}$, $I_{pd}^{30}$, $I_{ns}^{30}$, and $I_{nd}^{30}$, respectively. The indices for the seventh sequence in $y^{30}$ are highlighted; t and b refer to the top and bottom of the block of potential L-long matches in $y^{30}$; and h refers to the sequence that would immediately proceed to the query if it were in $y^{30}$.

FIG. 6 depicts a table of the running time (in seconds) for searching a query in panels containing 10,000 sites with an increasing number of haplotypes; the minimum length L was set to 1,000 sites.

FIG. 8 depicts a table of the running time (in seconds) for searching a query in panels containing 20,000 sites with an increasing number of sites; the minimum length L was set to 1,000 sites.

FIG. 9 depicts a table of the maximum resident set sizes (in GB) for different benchmarks.

FIG. 12 also shows the update of the w.(opposite of z[k]) pointers of the contiguous block of sequences above z with the opposite value as z at site k.

FIG. 19 shows the updating of the divergence value of z and z.below at position k based on position k+1. At column k, it is known that there is some sequence above z that matches until the divergence value of z in column k+1, because if the sequence is above z in column k+1 and it matches at site k, then it is above z in column k. The relative order of sequences that have the same value at site k is the same in columns k and k+1; the same applies for z.below and the divergence value of z.below.

FIG. 21 depicts an example of a PBWT panel (haplotype panel sorted by the reversed prefix order). All matches with a minimum length of 1 cM are separated by the sequence marked in red, in which $g[d[i]] > g[k] - L_g$ (k=12; d[i]=11, g[d[i]]=1.4, 1.4>1.5−1).

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The present invention includes the use of a PBWT method based on sorting the haplotype sequences based on their reversed prefix order. PBWT enables an efficient haplotype search among the haplotypes within a panel and has been applied for genotype phasing and imputation (Loh et al., 2016a, b). The proposed method enhances the use of PBWT by creating a system including a pool of PBWT genetic indexes with a haplotype ingestion engine and a haplotype query engine. The resulting system and method return highly accurate genealogical search results with a reduction in the amount of computing power consumed, thereby improving upon the prior art genealogical searching systems and PBWT systems.

Figure 1:
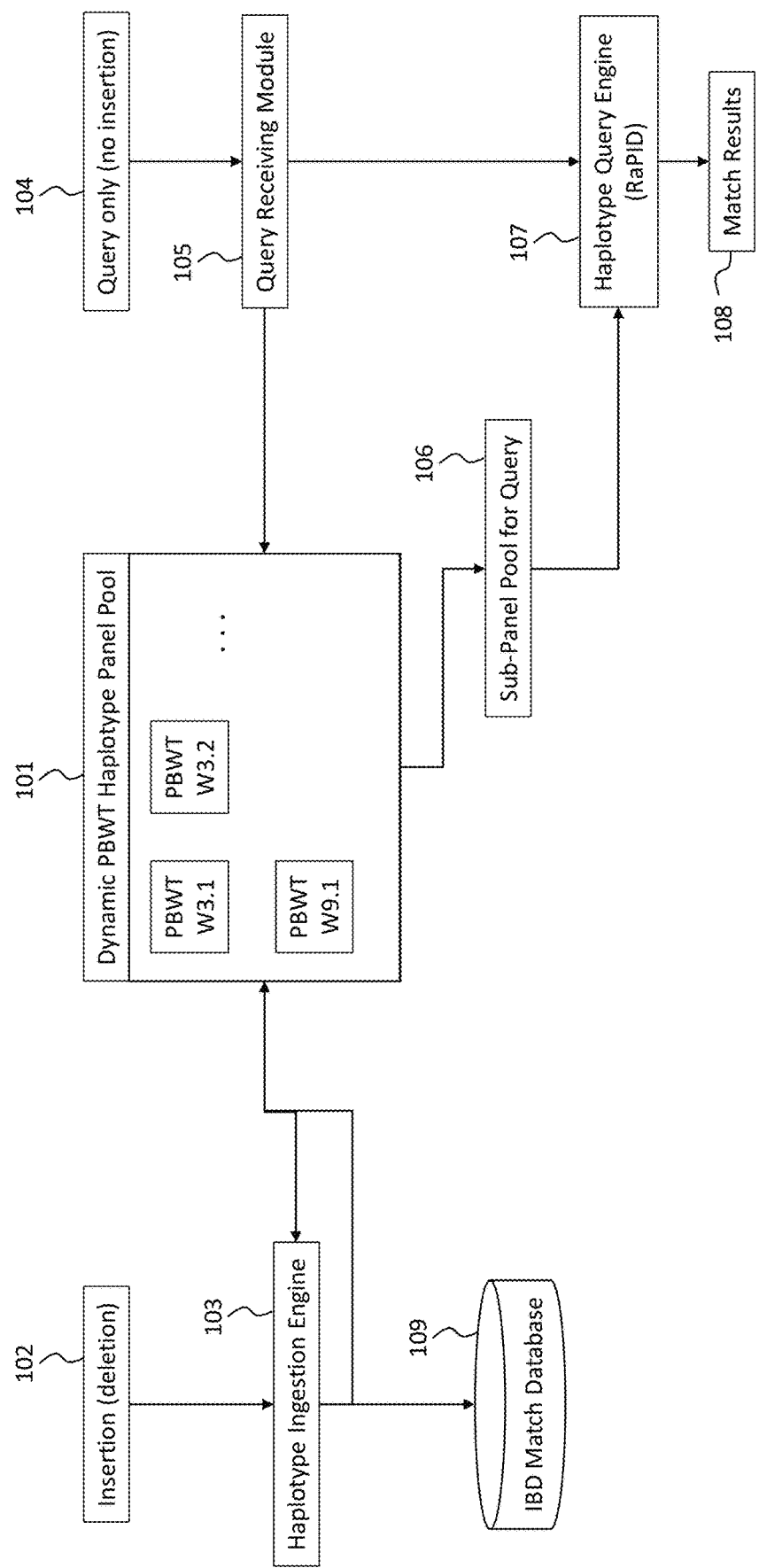
FIG. 1 depicts a genealogical search and classification system in accordance with an embodiment of the present invention.

FIG. 1 depicts an overview of the system, including three main components: a dynamic PBWT haplotype panel pool, a haplotype-ingestion engine, and a haplotype querying engine. The dynamic PBWT haplotype panel pool (also referred to as a panel pool) 101 is implemented as a computer memory, such as RAM or SSD, that supports persisted random-access. Panel pool 101 includes a number (e.g., 100) of PBWT haplotype panels, each over a random projection of the marker set of the original panel. The set of all projections is determined at the time of initialization of the entire haplotype pool. The design principle of the random projections is as first described in (Naseri et al. 2017) and later elaborated in (Naseri, Liu, et al. 2019). To allow flexibility, the set of projected panels were designed such that they are conditionally independent given the original panel. Each panel has a number of parameters, including its window size (sampling rate) and random seed. As a result, each panel has a set of desired characteristics including the detection power of IBD segments over all lengths ('wavelength of absorption') and the rate of false positive for a target population. To maximize the detection power, the selection of markers in the random projection is weighted by their minor allele frequency, which improves performance. To allow dynamic updates of panel pool 101, the PBWT data structure for each panel is a dynamic PBWT, called d-PBWT, first described in (Sanaullah, Zhi, and Zhang 2020). The d-PBWT data structure is stored in a persisted media. While it is possible to store the d-PBWT in computer memory, it can be costly. To curb the cost of large memory, a version of the d-PBWT can be implemented in a fast HDD, such as SSD.

Also included in the system of FIG. 1 is a haplotype-ingestion engine 103, which is a computer implementation of the insertion and deletion algorithms for dynamic PBWT, first described in (Sanaullah, Zhi, and Zhang 2020). For a request of adding a new individual, i.e., a pair of phased haplotypes 102, the engine first applies the set of projections in the PBWT pool to the new haplotypes, and then runs insertion algorithms to add the new haplotypes into each PBWT haplotype panel of panel pool 101. Deletion algorithms can also be run to remove haplotypes from panel pool 101. Pre-computed matches up to a certain length (such as 10 cM) may be stored in an IBD match database 109, which can return immediate results to customers. Beyond pre-computed matches (such as smaller matches of approximately 5 cM or 2 cM), the ingestion engine 103 and query engine 107 can be used in accordance with the system described herein.

The system receives requests to search a target haplotype against the panel for all long matches above a certain length cutoff. Upon receiving such a request 104, the system first calls a query receiving engine 105 to determine the subset of samples of the PBWT pool to activate. Second, the system projects the target onto the chosen PBWT haplotype panels 106. Third, a PBWT long-match query is performed for each of the chosen panels using the haplotype query engine 107. The haplotype query engine 107 is a computer implementation of one of the PBWT long match algorithms (Naseri, Holzhauser, et al. 2019; Sanaullah, Zhi, and Zhang 2020) and the merging algorithm (Naseri, Liu, et al. 2019). Finally, IBD segment calling outputs 108 are generated according to probability calculation.

In a real customer-facing implementation of a genetic genealogical system according to FIG. 1, the haplotype-ingestion engine 103 and the haplotype query engine 107 can be invoked together each time a new customer is inserted. Moreover, an existing user who already has been part of a genetic haplotype panel pool can refine a genetic genealogical search against the panel pool 101. Herein below, an overview of prior art PBWT methods is provided to frame the d-PBWT methods of the instant disclosure, as well as algorithms used to implement the system of FIG. 1 on genealogical datasets.

Overview of PBWT and Application of First Example of PBWT Improvement

PBWT (Durbin, 2014) facilitates an efficient approach to find all L-long matches, matches longer than or equal to a given length L, among the haplotypes in a panel. It also provides a fast approach to find the longest matches for a haplotype query in a panel. However, finding L-long matches to a query is of greater interest. For example, for a haplotype $s=s[0]s[1] \ldots s[N-1]$, $s[i,j]$ denotes the subsequence $s[i]s[i+1] \ldots s[j-2]s[j-1]$, and $|s|$ denotes the length of s (i.e., $|s|=N$). When any haplotype sequences are compared, it is assumed that the share the same sites, number of sites, and ordering of sites. To follow the notations of Durbin (2014), the haplotype matrix of X is defined as the matrix whose ith row is $X_i$.

Given a query haplotype z and a database of haplotypes $X=x_1, x_2, \ldots x_M$, where $|z|=|x_i|=N$ for any $x_i \in X$, it is the goal to find all L-long matches that are greater than or equal to length L between z, and all $x_i \in X$. It is assumed that there is an L-long match between z and $x_i$ from sites e to k if $k-e \geq L$, $e=0$ or $z[e-1] \neq x_i[e-1]$ and $k=N$ or $z[k] \neq x_i[k]$ (i.e., that the match from e to k between z and $x_i$ cannot be extended in either direction. To find L-long matches to a query, the position of the query in the PBWT panel at each site is identified. All of the possible L-long matches ending at a given site k will occur in contiguous blocks of haplotypes adjacent to the 'would be' position of the query in the panel sorted by the reverse of the prefix ending at site k. Hence, the neighboring sequences in the PBWT panel can be scanned to find L-long matches. The time complexity of PBWT-Query is $O(N+c(R-L+1))$, where R is the average length of the matches, and c is the total number of matches.

To increase search speed, LEAP (Linked Equal/Alternating Positions) arrays are used to reduce the search space of possible matches that terminate at each site k by skipping over haplotypes whose matches can still be extended to further sites. The LEAP arrays consist of arrays $I_{ps}^k$, $I_{pd}^k$, $I_{ns}^k$, $I_{nd}^k$, $I_{ps}^k$, $I_{pd}^k$, $I_{ns}^k$, and $D_{nd}^k$ for each site k, which are formally defined herein below. These arrays are generated from the PBWT matrix and independent from the query haplotype. This new approach is referred to as L-PBWT-Query, with a worst-case time complexity is O(N+c), where c is the number of L-long matches. The LEAP arrays can be pre-computed in O(NM) time, and require O(NM) space in main memory or hard disk. Therefore, the greatest utility of the approach is the use-case where the user has a large amount of hard disk or main memory space and a constant (or infrequently changing) database haplotype panel, and the user wants to perform many queries on the same panel. In this case, the database population needs only be pre-computed once to achieve subsequently fast.

The haplotypes in X sorted by the kth reversed prefix (i.e. by the reverse of sites 0 to k−1) as $y^k$, and the positional prefix array $a_k$ containing a permutation of the indices 0 to M−1 such that $y_i^k = X_{ak[i]}$. For every $y^k$, the contiguous block of haplotypes is referred to as $y_i^k, y_{i+1}^k, \ldots, y_{j-1}^k$, as $y_i^k$ through $y_j^k$; similarly, $y_i^k[k]$ through $y_j^k[k]$ refers to $y_i^k[k]$, $y_{i+1}^k[k] \ldots, y_{j-1}^k[k], y_j^k[k]$, etc. For example, if X={1001, 1111, 0100}, then, $y^3$={1001, 0100, 1111} and $a^3$={0, 2, 1}. Then, the PBWT matrix is referred to as the matrix whose ith column corresponds to the ith column of $y^i$.

The divergence array $d_k$ is defined such that $d_k[i]$ is the starting position of the longest match between $y_i^k$ and $y_{i-1}^k$ ending at k (Durbin, 2014), such that $d_k$ gives the starts of all the longest matches ending at a given k for any two adjacent haplotypes in $y^k$. The longest match between some $y_i^k$ and $y_j^k$ (i<j) ending at k begins at $$\max_{i<m\leq j} d_k[m].$$

The LEAP arrays of $I_{ps}^k, I_{pd}^k, I_{ns}^k, I_{nd}^k, D_{ps}^k, D_{pd}^k, D_{ns}^k$, and $D_{nd}^k$ for each site k are formally defined herein. For each $y^k[k]$, i.e. each column of the PBWT matrix, four indices are maintained: $I_{ps}^k, I_{pd}^k, I_{ns}^k$, and $I_{nd}^k$. $I_{ps}$ and $I_{ns}$ allow for jumping between equal values within each column of the PBWT matrix. Similarly, $I_{pd}$ and $I_{nd}$ allow for jumping around between differing values within each column of the PBWT matrix. The subscripts ps, pd, ns, and nd are shorthand for previous-same, previous-different, next-same, and next-different, respectively. If j is the largest index, such that $y_i^k[k]=y_j^k[k]$ and j<i, $I_{ps}^k[i]=j$. Said another way, $I_{ps}^k$ can be used to jump $y^k$ from a given haplotype to the closest preceding haplotype that has the same value at k. If j is the largest index, such that $y_i^k[k]\neq y_j^k[k]$ and j<i, $I_{pd}^k[i]=j$. Said another way, $I_{pd}^k$ can be used to jump $y^k$ from a given haplotype to the closest preceding haplotype that has the same value at k. If j is the smallest index, such that $y_i^k[k]=y_j^k[k]$ and j>i, $I_{ns}^k[i]=j$. Said another way, $I_{ns}^k$ can be used to jump $y^k$ from a given haplotype to the closest preceding haplotype that has the same value at k. Finally, if j is the smallest index, such that $y_i^k[k]=y_j^k[k]$ and j>i, $I_{nd}^k[i]=j$. Said another way, $I_{nd}^k$ can be used to jump $y^k$ from a given haplotype to the closest preceding haplotype that has the same value at k Although these indices facilitate the ability to skip unnecessary haplotypes during the search, when jumping between haplotypes, it is necessary to know if the block of potential L-long matches terminated in the skipped haplotypes. If any divergence value for the skipped haplotypes is larger than L−k, it is known that the query cannot have an L-long match ending at k to the haplotype that was jumped to. Therefore, four additional arrays are maintained: $D_{ps}^k, D_{pd}^k, D_{ns}^k$, and $D_{nd}^k$, which are natural counterparts to $I_{ps}^k, I_{pd}^k, I_{ns}^k$, and $I_{nd}^k$. Each of these arrays stores the largest divergence value between the haplotypes that are skipped, depending on the index that was used to jump. For example, if $I_{ps}^k[i]=j$ is used to jump from $y_i^k[k]$ to $y_j^k[k]$, $D_{ps}^k[i]$ provides $$\max_{i<r<j} d_k[r];$$

similarly, if $I_{ns}^k[i]=j$ is used to jump from $y_i^k[k]$ to $y_j^k[k]$, n[i] provides $$\max_{i<r<j} d_k[r].$$

$D_{ps}^k, D_{pd}^k, D_{ns}^k$, and $D_{nd}^k$ are undefined when fewer than two haplotypes are skipped using $I_{ps}, I_{pd}, I_{ns}$, and $I_{nd}$, respectively; in such cases, divergence arrays can be used directly.

Figure 2:
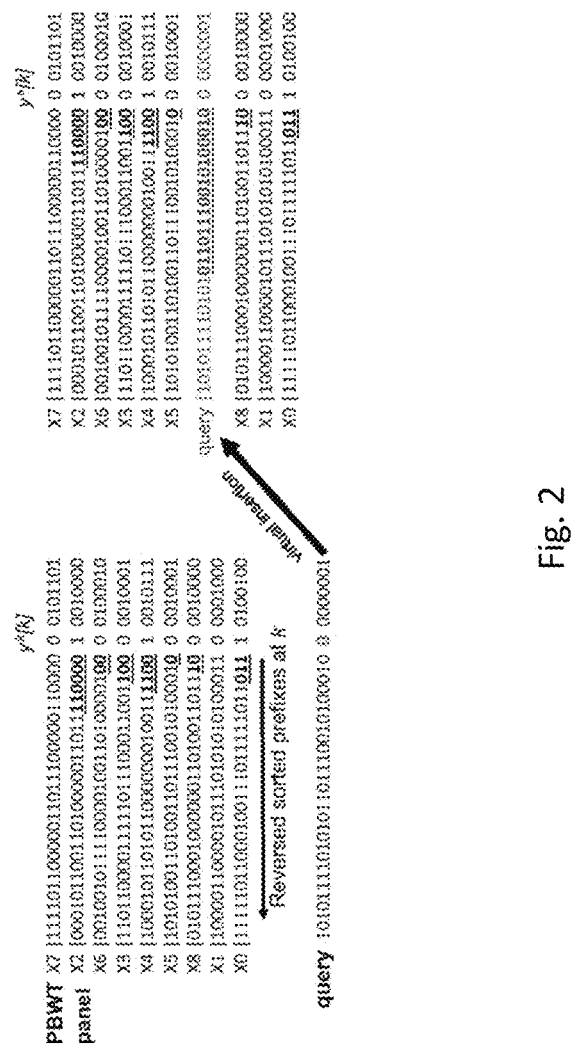

FIG. 2 shows a simple example of virtually inserting a query haplotype to the PBWT panel. The position of the new haplotype at each site is adjacent to the longest match at the site k. Durbin (2014) proposed an efficient algorithm to find all set-maximal matches between a query z and a panel X, UpdateZMatches [Durbin's Algorithm 5 (Durbin, 2014)]. A set-maximal match (Durbin, 2014), between z and some $x_i \in X$ is defined as an L-long match (L≥1) between z and xi from e to k such that there does not exist a match between z and any other $x_j \in X$ (i≠j) from e' to k' where e'<e or k'>k. Simply, the match between z and $x_i$ is set-maximal if it cannot be extended in either direction, and z does not have a larger match to any other haplotype in X whose indices enclose the indices of its match to $x_i$. To find all set-maximal matches at k, UpdateZMatches computes three values: $f_k, g_k$, and $e_k$, such that z has a set-maximal match to $y_{fk}^k$ through $y_{gk-1}^k$ from $e_k$ to k if $y_{fk}^k[k]$ through $y_{gk-1}^k[k]\neq z[k]$. UpdateZMatches computes $f_k, g_k$, and $e_k$ based on $f_{k-1}, g_{k-1}$, and $e_{k-1}$, respectively. To follow the notations of Durbin (2014), w is defined such that w(k, i, 0)=$u_k[i]$ and w(k, i, 1)=$c_k+v_k[i]$, where $u_k[i]$ is the number of zero values at site k in $y_0^k$ through $y_{i+1}^k$, $v_k[i]$ is the number of one values at site k in $y_0^k$ through $y_{i-1}^k$, and $c_k$ is the total number of zeroes at site k.

$y_{i+1}^k$ through $y_j^k$ all have a match to $y_i^k$ of at least length k−$d_k[m]$, and $y_i^k$ through $y_{j-1}^k$ all have a match to $y_j^k$ of at least length k−$d_k[m]$. This implies that if some haplotype $y_i^k$ in X is picked, it is known that all matches to $y_i^k$ ending at k of length greater than or equal to L occur in some block $y_t^k$ through $y_b^k$ in $y^k$ such that t<b, 0≤t≤i+1, i−1≤b<<M and $$k - \max_{t<m\leq b} d_k[m] \geq L.$$

It follows that all matches to X ending at k, whether from an external query haplotype or internal haplotype, occur in a contiguous block at $y^k$.

All matches to z ending at k of length greater than or equal to L occur in a contiguous block $y_{t_k}^k$ through $y_{b_k}^k$ in $y^k$ such that $t_k<b_k$, 0≤$t_k$≤$h_k$, $h_k$−1≤$b_k$<M and $$k - \max_{t_k<m\leq b_k} d_k[m] \geq L.$$

What is left, then, is to find the smallest index $t_k$ and largest index $b_k$ that enclose the block of haplotypes with potential L-long matches. The L-long matches are referred to as "potential" because each $y_{t_k \le i \le b_k}^k$ is only a match if $y_i^k[k]=z[k]$, but not an L-long match, as the end of the match can be extended, i.e. $y_i^k[e_k, k+2]$ matches $z[e_k, k+2]$. $d_z^k$ is defined to be the smallest value, such that $y_{h_k}^k[d_h^k, k]$ matches $z[d_z^k, k]$. $d_z^k$ and $d_k$ can be used to scan up $y^k$ beginning at $y_{h_k-1}^k$ until $y_{t_k}^k$ is identified, except in the case where $t_k=h_k$, printing L-long matches along the way. Similarly, $d_h^k$ and $d_k$ can be used to scan down $y^k$ beginning at $y_{h_k}^k$ until $y_{b_k}^k$ is identified, except in the case where $b_k=h_k-1$ printing L-long matches along the way. Specifically, the method can continue scanning in either direction, so long as $k-d_k[i] \ge L$ for the particular $y_i^k$ being iterated through, and L-long matches can be printed between z and $y_i^k$ so long as $z[k] \ne y_i^k[k]$. Although scanning up, if $t_k \le h_k-2$, the match between z and a particular $y_i^k$ begins at max $$\left(d_z, \max_{i-1 \le m \le h_k-1} d_k[m]\right).$$

Similarly, while scanning down, if $b_k > h_k$, the match between z and a particular $y_i^k$ begins at max $$\left(d_h, \max_{i-1 \le m \le h_k-1} d_k[m]\right).$$

Figure 3:
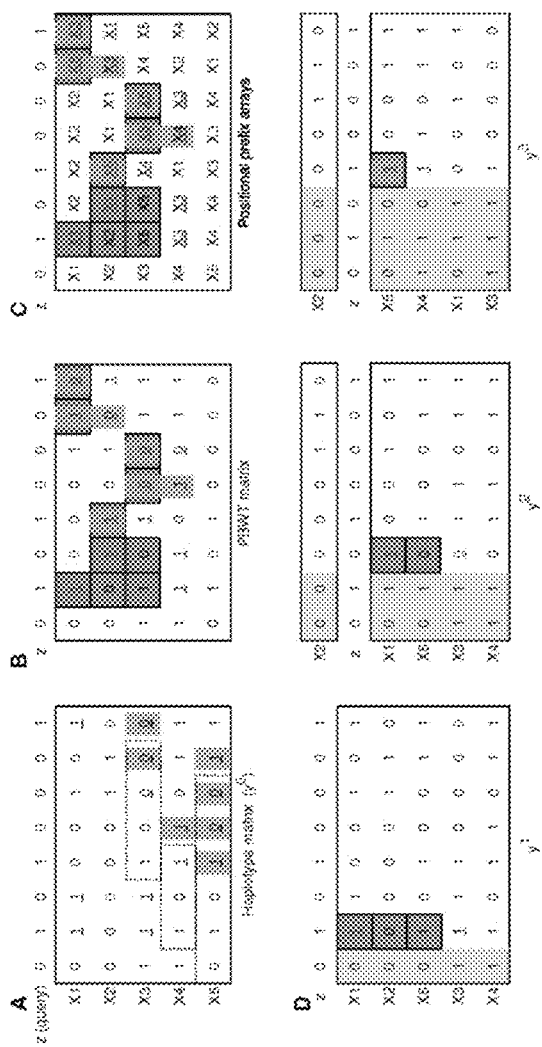
FIG. 3 depicts an example of searching for L-long matches of length ≥3 in a panel with five haplotypes comprising eight sites. Section A of FIG. 3 depicts the haplotype matrix ($y^0$) and the query z. Section B of FIG. 3 depicts the PBWT matrix, with the ith column in the PBWT matrix corresponding to the ith column of $y^i$. Section C of FIG. 3 depicts the positional prefix arrays, with each row depicting the positional prefix array $a_k$. Each positional prefix array $a_k$ contains the permutation of indices 0 to N−1 such that $y_i^k = X_{a_k[i]}$. Section D of FIG. 3 depicts the $y^k$'s for k=1, 2, 3. The haplotypes in X are sorted by the kth reversed prefix (i.e. by the reverse of sites 0 to k−1) and are referred as $y^k$. The prefixes used to sort are shaded in gray in $y^1$, $y^2$ and $y^3$. The blocks of potential set-maximal matches ending at k are labeled in purple, the index of the haplotype that immediately proceeds to z is highlighted as red, and the intervals of potential L-long matches ending at each site are highlighted in lime green. The f and g values which enclose the block of potential set-maximal matches are underlined.

FIG. 3 illustrates searching for L-long matches for L=3. For clarity, example $y^k$'s for k=1, 2, 3 have been included, the reverse prefixes that are used to sort the rows of the haplotype matrix highlighted in grey, and the sorted order of z is included in these panels. The key idea of the approach is to scan through each site k from 0 to N to find the would-be position of the query z in $y^k$. Then, the method can scan up and down site k in $y^k$ to search for L-long matches that end at that site. First, at each site k, the block of potential set-maximal matches ending at k is found, and is labeled in purple in FIG. 3. If z were in $y^k$, it would occur at the beginning or end of this block. In this example, z always happens to be at the beginning of the purple blocks, but it can also occur at the end. As the method scans through this block, the output is an L-long match ending at each green position if, at that position, there is a mismatch between that individual and the query.

The time complexity of computing $f_k$, g and $e_k$ is O(N) across all k (Durbin, 2014). For a given site, all M haplotypes may be scanned in search of $t_k$ and $b_k$. If there is a block of matches that does not terminate at each site, the entire block still must be scanned. As this scanning occurs for N sites, the time complexity of PBWT-Query is O(N+c(R−L+1)), where R is the average length of the matches and c the total number of matches.

Although searching for $t_k$ and $b_k$, the smallest and largest indices that contain potential L-long matches, every $y_i^k$ scanned through where $z[k]=y_i^k[k]$ (i.e. the match can be extended further) is unnecessary work. Therefore, if the search at each site is restricted to only those $y_i^k$ where $z[k] \ne y_i^k[k]$, the time complexity of searching for $t_k$ and $b_k$ across all sites to O(N+c) can be improved, where c is the number of L-long matches. This improvement is achieved by maintaining a data structure that allows for efficient jumping between $y_i^k[k]$ of the same k, for i=0 to M−1 and k=1 to N−1. Again, the key idea is to jump around between only those $y_i^k[k]$ where $z[k] \ne y_i^k[k]$. For bi-allelic data, if $z[k]=1$, it is preferred to move around $y_i^k[k]$ that equal to 0, and similarly, if $z[k]=0$, it is preferred to move around between $y_i^k[k]$ that equal to 1, to find matches that end at k+1.

Using the data structure, the procedures can be modified to scan up and down in search of $t_k$ and $b_k$ once $h_k$ has been identified. Namely, when scanning up, $I_{ps}^k$ or $I_{pd}^k$ can be used to find the first $y_i^k(i \le h-2)$ such that $z[k] \ne y_i^k[k]$, if such exists. Then, if necessary, $I_{ps}^k$ can be used to keep searching only through haplotypes that differ from z at site k. Similarly, when scanning down, $I_{ns}^k$ or $I_{nd}^k$ can be used to find the first $y_i^k(i \ge h+1)$ such that $z[k] \ne y_i^k[k]$, if such exists. Then, if necessary, $I_{ns}^k$ can be used to keep searching only through haplotypes that differ from z at k.

Figure 4:
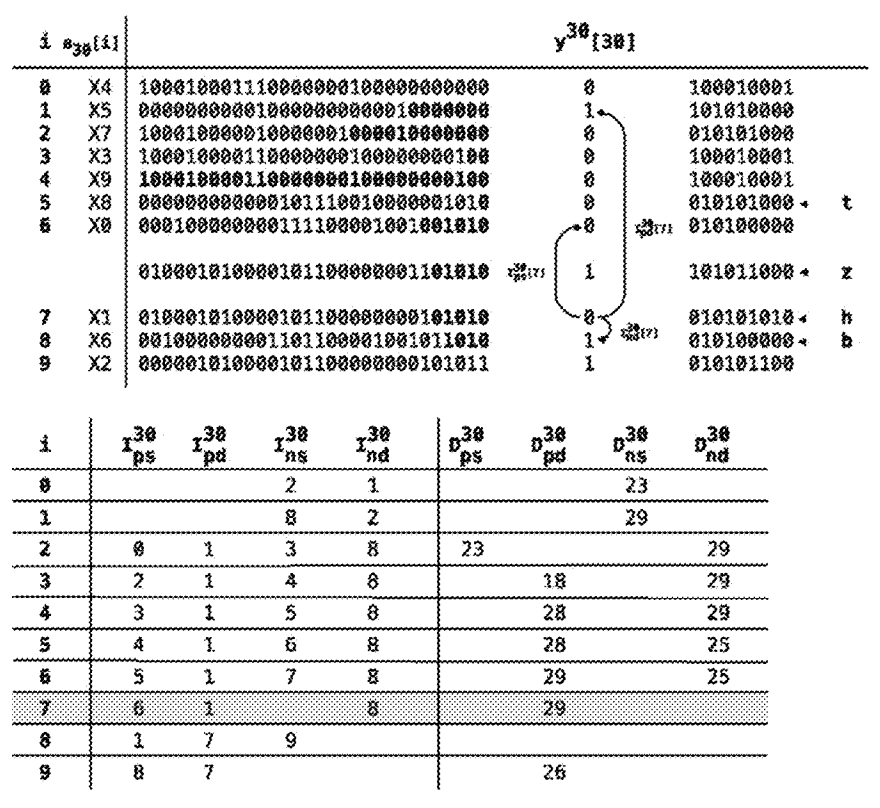

FIG. 4 demonstrates $y^{30}$ for an example genotype panel, along with the indices used to facilitate efficient query search. In the panel, t and b refer to the indices that define the block of haplotypes $y_t^{30}$ through $y_b^{30}$ where all L-long matches for L=4 ending at site 30 may occur. Within that block of haplotypes, those $y_i^{30}$ are of interest where $y_t^{30}[30] \ne z[30]$. Typically, it would be required to scan up from $y_{h-1}^{30}$ to find t and scan down from $y_h^{30}$ to find b, and without the indices, scanning may be required through the entire column, representing a worst-case O(M) operation, in which, across all sites, O(NM) operations may be required. However, with the indices of the instant method, those sequences where the match ends at 30 are traversed; so, at site 30, the scanning up and down processes are improved to worst-case O (the number of matches ending at 30), and therefore, across all sites, the runtime is improved to worst-case O(N+c), where c is the number of L-long matches.

As before, the time complexity of computing $f_k$, $g_k$ and $e_k$ is O(N) across all k (Durbin, 2014). Now, the worst-case time complexity for scanning for $t_k$ and $b_k$ across all sites is O(N+c), where c is the number of L-long matches. So, the total worst-case time complexity for L-PBWT-Query is O(N+c), which is independent from the number of haplotypes M. Although the querying approach has a runtime linear in N and the number of L-long matches, the approach assumes that the PBWT, I matrices and D matrices for X are pre-computed and stored in the hard disk. These can be computed in O(NM) time, and they occupy O(NM) space in the hard disk. Specifically, if X occupies NM memory, the additional I and D matrices occupy roughly 8 NM memory.

Results

Two versions of L-PBWT-Query were implemented: L-PBWT-Query (Memory-Mapped), in which all of the pre-computed data structures are accessed using memory-mapped files using Boost libraries; and L-PBWT-Query (Memory-Extensive), in which all of the pre-computed data structures are loaded into main memory. To clarify, L-PBWT-Query (Memory-Mapped) does not load all of the panel and data structures in main memory at once. Instead, parts of the panel and data structures are loaded from the appropriate files into memory in a 'lazy loading' fashion, i.e. as they are needed. Therefore, using memory-mapped files reduces I/O operations. This mechanism provides a relatively fast alternative to access the panel and data structures, especially if a panel has been recently queried by queries relatively similar to subsequent queries, which is referred to as 'warming up' a panel. When a panel is warmed up, relevant portions of the panel and data structures (a relatively small subset of the overall panel and data structures) have already been loaded into main memory and mapped to virtual memory, for faster subsequent access.

A large haplotype panel was simulated using the Markovian Coalescent Simulator (MaCS) Chen et al. (2009) with the command macs 500001 2000000-t 0.001-r 0.001-h 1e2 and extracted subsets of the panel for the benchmarking. For the purpose of benchmarking, PBWT-Query (Memory-Extensive) and Exhaustive Search were implemented. Exhaustive Search scans across the entire length of sites for each pair of the query and a haplotype in the panel, which has O(NM) time complexity. For all of the benchmarks, the following protocol was used: when running L-PBWT-Query (Memory-Mapped), for a given panel, a panel was always warmed up with three runs on the particular query, then averaged the runtime of three additional runs. When running PBWT-Query (Memory-Extensive), L-PBWT-Query (Memory-Extensive) and Exhaustive Search, the runtimes of three runs were averaged.

Figure 5:
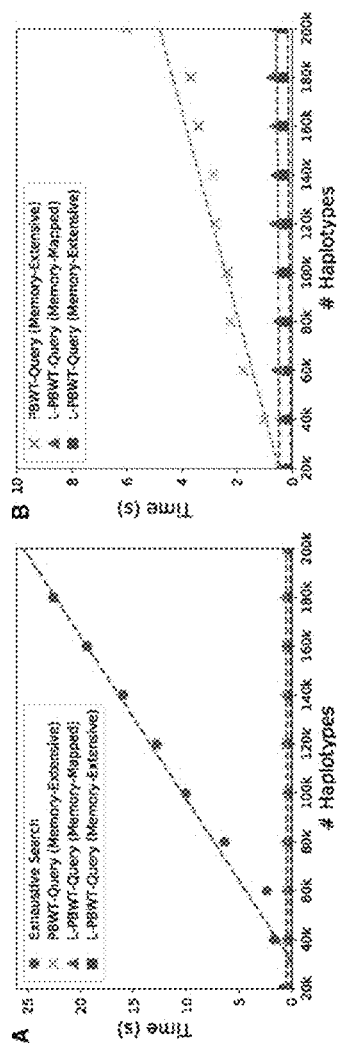
FIG. 5 graphically depicts the running time (in seconds) for searching a query in panels containing 10,000 sites with an increasing number of haplotypes while keeping the number of matches constant (in graph A) and with an increasing number of matches (in graph B).

First, it is desired to verify that the runtime of PBWT-Query and L-PBWT-Query, in practice, is truly independent from the number of haplotypes. To that end, a benchmark was developed which is referred to as the increasing haplotypes benchmark. FIG. 5 and FIG. 6 show the results of the increasing haplotypes benchmark, respectively, which support the assertion that the runtime of the approach is independent from the number of haplotypes. For this benchmark, panels were tested in which the number of haplotypes in the panel was successively increased by a constant amount (from 20,000 to 200,000 haplotypes in steps of 20,000). In the first experiment, the number of sites (10,000) and the number of matches (25,359) were kept constant for the added haplotypes (section A of FIG. 5 and FIG. 6). The minimum length of match L was set to 1000. For the Exhaustive Search, run time increases roughly linearly with the number of haplotypes (M). The runtime of the memory-mapped implementation stays roughly constant, even as the number of haplotypes are increased ten times. When compared with L-PBWT-Query (Memory-Extensive), there appears to be some constant overhead associated with fetching data from memory-mapped files, instead of cache or main memory. PBWT-Query runtime is similar to L-PBWT-Query as the number of matches remains constant. In the second experiment, the number of haplotypes were increased, and the number of matches increases linearly (section B of FIG. 5 and FIG. 6). Both L-PBWT-Query implementations show a better runtime compared with PBWT-Query with increasing number of haplotypes and increasing number of matches.

Figure 7:
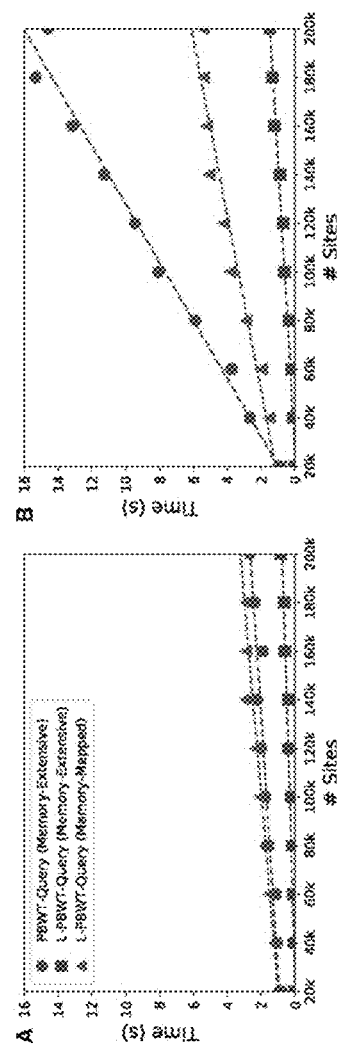
FIG. 7 graphically depicts the running time (in seconds) of searching for a query in panels containing 20,000 haplotypes with an increasing number of sites while keeping the number of matches relatively constant (~70 000 matches, in graph A) and with an increasing number of matches in a linear manner with the number of sites (in graph B).

Additionally, it is desired to concretely investigate the additive effect of increasing sites and increasing matches on the runtime of PBWT-Query and L-PBWT-Query. To that end, a benchmark was developed which is referred to as the increasing sites benchmark. FIG. 7 depicts a plot of the increasing sites benchmarks, and FIG. 8 gives the runtimes of those benchmarks. Two benchmarks were performed: one in which the number of sites was successively increased (from 20,000 to 200,000) while keeping the number of matches constant (section A FIG. 7), and another in which the number of sites was successively increased (from 20,000 to 200,000) while the number of matches increases linearly with the number of sites (section B of FIG. 7). FIG. 7 shows that the runtime of the approach increases as expected, linearly with the number of sites and matches. As before, there is some constant overhead associated with fetching from memory-mapped files instead of main memory. All benchmarks were run on a 2.1 GHz server with 500 GB of RAM. The maximum resident sizes for the benchmarks are included in FIG. 9.

Example 1—Applying PBWT-Query and L-PBWT-Query on the UK Biobank Data

PBWT-Query and L-PBWT-Query were tested on the UK Biobank data (487,409 participants and 974,818 haplotypes for autosomal chromosomes) (Bycroft et al., 2018) to demonstrate their utility on real data. The UK Biobank dataset includes pairwise kinship coefficients between individuals computed using the KING toolset (Manichaikul et al., 2010). According to the KING tutorial, the kinship coefficient ranges [0.177, 0.354], [0.0884, 0.177] and [0.0442, 0.0884] denote first-, second- and third-degree relationships, respectively. Here, a first-degree relationship refers to a parent-offspring or full-sibling relationship, a second-degree relationship includes half-siblings, avuncular pairs and grandparent—grandchild pairs, and a third-degree relationship includes the first-cousins (Manichaikul et air, (2010).

The aim is to investigate whether potential genetic relationships from the UK Biobank data can be inferred by searching for exact matches using PBWT-Query or L-PBWT-Query. Because true IBDs can be disrupted by mismatches, the sum of the lengths of L-long matches between a pair of individuals was tested as a potential signal to differentiate first-, second- and third-degree relationships from each other, and from a background population. Two hundred individuals (400 haplotypes) which had genetic relationships within the UK Biobank data were chosen as queries. As a representative sample of the background population, one thousand individuals were randomly chosen from the UK Biobank excluding the 200 query individuals. The two hundred individuals were queried against the entire UK Biobank data for exact matches of length ≥700 SNPs in Chromosomes 1 through 22. This match length cutoff was chosen by following the precedent of 23andMe®, whose simulations show that first, second and third cousin relationships can be reliably detected by haplotype matches of length ≥700 SNPs and 7 cM across all chromosomes. If the detection power is considered as the percentage of related pairs with any matches of length ≥700 SNPs, there is a 100% detection power in detecting potential first- and second-degree relationships by searching only in Chromosome 1. The detection power for first, second and third-degree relationships using all autosomal chromosomes is 100%. The queries were run using PBWT-Query and L-PBWT-Query (Memory-Extensive) on a 2.5 GHz server with 15 TB of SSD and 6 TB of RAM. The average time for running L-PBWT-Query a single query (one haplotype) on Chromosomes 1 through 22 is 6 s and for PBTW-Query 20s, discounting the time to load the L-PBWT-Query data structures into memory. The maximum resident set size for L-PBWT-Query was 4.7 TB, and 2.4 TB for PBWT-Query.

Figure 10:
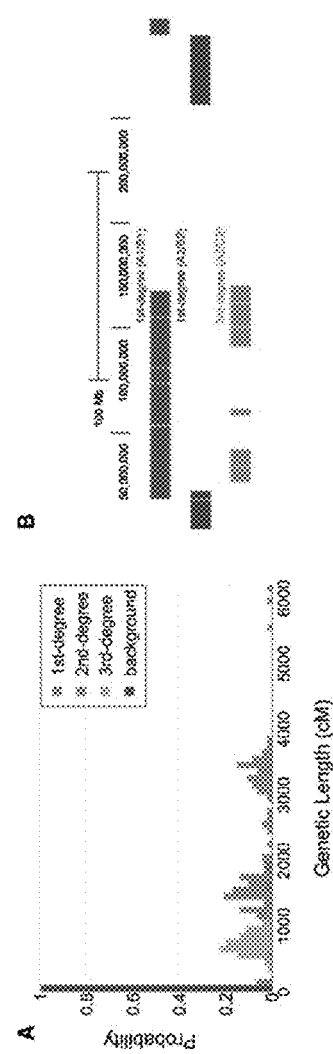
FIG. 10 graphically depicts the probability distributions of the sum of L-long matches (in cM, or centimorgans) between the query and related individuals (first-, second- or third-degree), and random individuals in the UK Biobank data, with relatedness computed using KING (in graph A); and an example of detected identical segments in Chromosome 1 (in bps) for an individual with at least two relatives (first- and third-degree relatives) in the UK Biobank data (in graph B).

There is a promising separation between the three degrees of relatedness and the background population. Section A of FIG. 10 shows that the sum of the lengths of L-long matches between a pair of individuals is a capable signal to differentiate first-, second- and third-degree relationships from random pairs picked from the background population, and to filter potential first- second- and third-degree relationships for further processing. Section B of FIG. 10 shows an example of detected identical segments in Chromosome 1 between an individual (A) and two of their relatives (B and C) in the UK Biobank data. The two haplotypes for each individual are distinguished by 1 and 2 (e.g. A has haplotypes A1 and A2). The total length of the segments shared with the first-degree relative is significantly larger than those shared with the third-degree relative. The AUC values were computed to differentiate three degrees of relationships using the sum of the lengths of the shared segments. The AUC value between first- and third-degree relationships is 0.98, and AUC value between first- and second-degree relationships is 0.96. There are a few outliers in the second-degree relationships; however, the AUC value between the second- and third-degree relationships is 90%. Thus, identical segments interrupted due to genotyping or phasing errors can be used to infer the related individuals, and to estimate the degree of relatedness between closely related individuals, without careful post-processing of the interrupted matches.

Conclusion

Two efficient algorithms, PBWT-Query and L-PBWT-Query, are proposed for finding all L-long matches between a query haplotype and a panel. The time complexity of L-PBWT-Query does not rely on the number of haplotypes in the panel, which enables on-line genealogical search in large cohorts. Furthermore, the memory-mapped version of the algorithm, L-PBWT-Query (Memory-Mapped), facilitates fast search when extensive main memory is not available, in exchange for a slightly increased running time. PBWT-Query shows similar runtime to L-PBWT-Query as the number of matches remains constant with the increasing number of haplotypes. However, the difference in efficiency becomes more obvious with the increasing number of matches.

L-PBWT-Query (Memory-Mapped) does not require loading the entire panel into the main memory in order to facilitate a fast search. The tradeoff, however, is an increased running time due to increased I/O operations. The running time of the L-PBWT-Query (Memory-Mapped) version is slightly worse than L-PBWT-Query (Memory-Extensive), but L-PBWT-Query (Memory-Mapped) is more practical if extensive memory resources are not available.

The L-PBWT-Query was applied to ~500 k individuals from the UK Biobank data and the method provided for the detection of close relatives of query individuals. The running time for all autosomal chromosomes in the UK Biobank data is only a few seconds using a single CPU. The results show that very close relatives can be easily found by L-PBWT-Query. PBWT-Query was also run on the UK Biobank data. Although the memory usage for PBWT-Query was lower than L-PBWT-Query, the run time was moderately worse.

Example 2—Rapid Projection for IBD Detection (RaPID)

Figure 11:
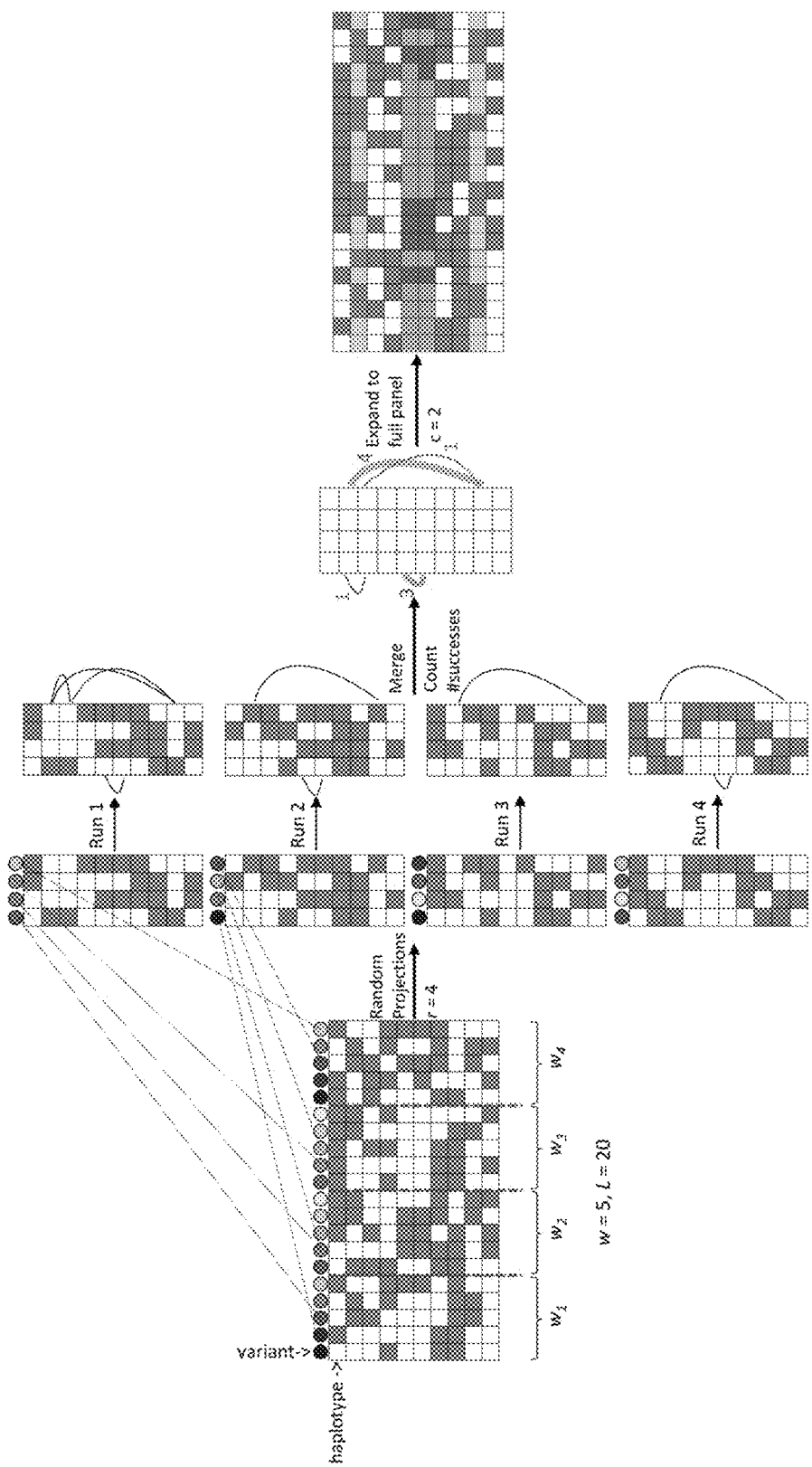
FIG. 11 is a schematic overview of a Random Projection for IBD Detection (RaPID) method in accordance with an embodiment of the present invention.

Using PBWT, fast methods for IBD segment detection can be used to efficiently index population genetic sequences, which will be referred to herein as RaPID methods. The key idea of RaPID is that the problem of approximate high-resolution matching over a long range can be mapped to the problem of exact matching of low-resolution subsampled sequences with high probability. Specifically, given a panel of phased haplotypes as an input, RaPID first produces multiple low-resolution random projections of the original sequences, runs PBWTs finding exact matches over each projection, and then combines the results (FIG. 11). One main advantage of RaPID over existing methods is that there is a principled way of determining parameter configurations which allows for proper control of detection power and accuracy for the detection of IBDs over a certain target length, given particular marker density and error rates.

The random projection with PBWT is a general scheme of translating the high-resolution sequences into multiple low-resolution ones, and the approximate high-resolution match can be translated into high probability low-resolution exact matches. The choice of projection function follows the rationale that it should translate similar sequences to the same sequence with high probability while translating dissimilar sequences to the same sequence with a low probability. Separation of the two probabilities can be guaranteed by multiple runs of random projection and PBWT.

In RaPID, random projection is chosen by simply picking a random site from a window of fixed size. Parameters of RaPID include (r, c, w), where r denotes the number of runs, c ($\leq$r) denotes the minimum number of runs that a match should be found in order to be considered, and w denotes the number of SNPs per window. Given an input panel, the sequencing error rate E and the chances of collision of projections from unrelated sequences p can be determined given w. For any target IBD segment length l in terms of the number of SNPs, probability calculations were used to choose these parameters to ensure high detection power and low rate of false positives.

Assuming the genotyping errors are randomly distributed and given the density of marker, a strategy to select the parameters to target IBD segments of a given length is provided. The random projection is run r times, with each window containing w SNPs, and then the PBWT is ran to consider any returned match with $\geq$S SNPs as a 'hit.' The number of hits follows a binomial distribution for both true IBDs and non-IBDs. For a true IBD segment pair of length l with identical original sequence, an error rate of $\varepsilon$ ($<<$1) is assumed, including both mutation and genotyping error rate. The binomial probability in each run is $$(1-\varepsilon)^{\frac{S}{w}} \approx e^{\frac{S\varepsilon}{w}}, \text{ or } X_T \sim \text{binomial}\left(r, e^{-\frac{S\varepsilon}{w}}\right).$$

For a random pair of segments, the probability of having a hit with at least S/w—window is $$p^{\frac{S}{w}},$$

where p=1−p is the probability that a randomly chosen pair of chromosomes would share the projected sequencing in a window, or $X_F$~binomial $$\left(r, p^{\frac{S}{w}}\right),$$

where $X_T$ denotes the number of runs that a true IBD segment has been reported, and where $X_F$ denotes the number of runs that a false IBD segment has been reported. The success of random projection PBWT relies on the choice of a parameter c, such that the power Pr ($X_T \geq$c) is high, while the expected number of false positives $$\binom{N}{2}$$

Pr ($X_F \geq$c) is low. Note that p is a population genetics parameter determined by haplotype frequency, which varies from region to region. ε is determined mainly by genotyping error rate as mutation rates are typically much lower. ε is in the range of 0.001-0.01.

The parameters, the number of runs r, and the minimum number of passes c will determine the appropriate range of subsampling values that will result in high true-positive and low-positive probabilities. The value of r should be sufficiently large to show a clear separation between true and false positives, at the same time be small enough to curb the run time burden.

A numerical optimization is used to calculate the optimal parameters for an input haplotype panel for a target IBD length. An objective function to be minimized using true-positive $t_p$ and false-positive $f_p$ rates defined as:

Given λ, M, d, L, and ε, find θ={r, c, w} s.t.f (θ)=λ$f_p$-$f_p$ is minimized where $$t_p(\theta) \sim \text{binomial}\left(r, c, e^{-\frac{L\varepsilon}{w}}\right), t_f(\theta) \sim \text{binomial}\left(r, c, p^{\frac{L}{w}}\right),$$

and p=g(w). M denotes the number of haplotypes, d the marker density, L the minimum length in terms of the number of sites, and ε the expected genotyping error rate. The parameters $t_p$ and $f_p$ can be calculated using binomial distributions using additional parameters that are to be estimated, namely r, c, w, and p. λ adjusts the weight of false-positive rates. The number of total comparisons is set as $$\lambda = \frac{M(M-1)}{2}.$$

As noted above, r denotes the number of runs, c the number of successes, and w the window size. The parameter p denotes the random probability of a match. The true-positive rate (or detection power) is independent of the parameter p. True positive is primarily a function of d, L, ε, r, c, and w. As the number of runs (r) and the window size (w) increase, the true-positive rate should also increase. However, large window sizes or the number of runs (while keeping c constant) will result in higher false-positive rates and consequently lower accuracy. False positive rates depend on the expected random probability of a match (p) rather than the error rate. Furthermore, p can vary depending on the selected window size.

Given a dataset, p and w are functionally linked, and their link p=g(w) is determined by the input data as follows: p is a function of minor allele frequencies, assuming the number of single matches at random is significantly higher than those within true IBD segments, and can be defined as p=p²+(1-p)², where p denotes the minor allele frequency (MAF) of the SNP that is sampled from the window. Since a weighted random projection is used by giving more weight to the sites with the higher MAF, the expected MAF of the selected SNP is calculated for each window. As a result, the MAF may change by using different window sizes. On the other hand, the changes of expected MAF are small at a sufficiently large window cutoff in population data. For example, to choose a more conservative value for p, the 10th percentile of expected MAF (90th percentile of ρ) can be chosen along the chromosome.

The objective function is optimized as follows: first, the input panel is scanned and M, d, and the functional link g are determined. Second, r=10 and c=2 are chosen to provide an optimal solution with $t_p$≈1 and $f_p$≈0 (determined by prior experimentation). The parameter ε is set to equal 0.0025 as this is the maximum expected error rate and often used by existing methods. Third, all window sizes are scanned from 1 up to the maximum window size of 500 as the permissible range. If more than one window size is available in the permissible range, a window size is manually chosen by the following practical concerns. For example, if there is a miscalculation of p and its value is close to 1, then smaller window sizes would not cause higher false-positive rates. Hence, it is recommended to pick smaller values within the permissible range, especially for panels containing a high number of sites with very rare minor alleles, e.g., sequencing data. Finally, after choosing the window size, it is verified that the corresponding $t_p$≈1 and $f_p$≈0. If this is not verified, a larger r is chosen, and the process is repeated.

To estimate the parameters, the minimum length of IBD segments is given. Each run of PBWT algorithm produces a list of the matches that exceed a given length. The length is defined in terms of consecutive variant sites. Assuming the variant sites are distributed evenly in the chromosome, the average number of variant sites to gain the minimum length can be computed by S=⌊l×d⌋, where l is the minimum IBD length in Mbps, and $$d = \frac{T}{\text{chr\_length}},$$

where T denotes the total number of variant sites in the chromosome, and chr_length denotes the length of the chromosome in Mbps or cM. To find IBD segments larger than a given length in cM in real data with various recombination rates, RaPID can handle genetic and genomic distance at the same time. The parameters can be selected using the minimum target length in terms of Mbps. The genomic distance in terms of Mbps can be picked as the minimum physical distance to cover at least 90% of the length in cM. RaPID will search for the matches greater than the given length in terms of Mpbs and ignore those that are shorter than the given length in terms of cM.

Results 4,000 haplotypes with a length of 10 Mbps were generated using a simulator, assuming a population with a history similar to that of the current European population with a mutation rate of $1.3 \times 10_{-8}$ per base pair per generation and a constant recombination rate of 1 cM per 1 Mbps, which results in a heterozygosity rate similar to that of the UK population data. The genotyping errors were introduced in the generated haplotypes at a rate of 0.0025 per genotype for each haplotype. The true IBDs were determined as uninterrupted sharing of the most recent common ancestor above a certain length.

Figure 12:
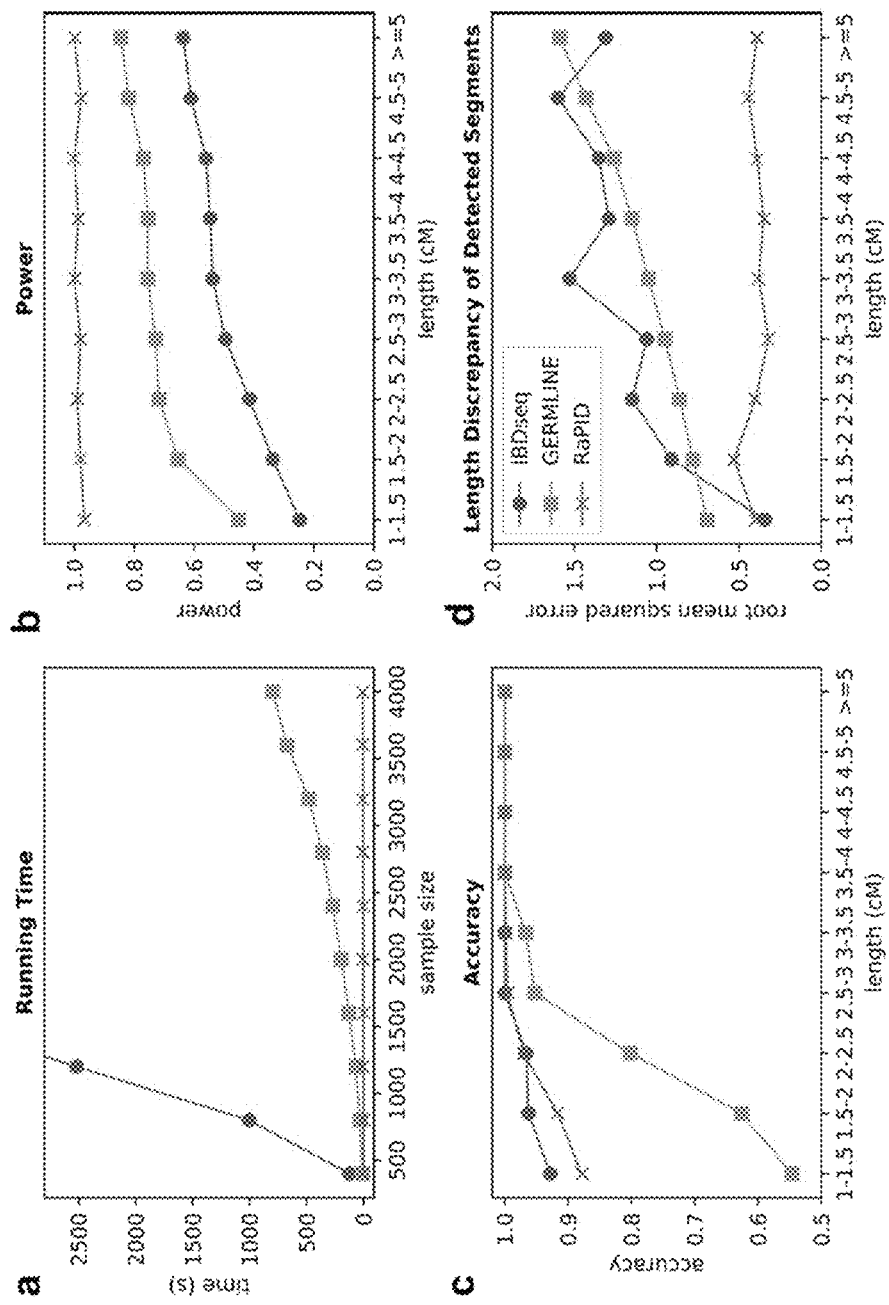
FIG. 12 graphically depicts benchmarking results of the RaPID method of FIG. 11 compared to prior art IBD detection methods, showing the running time (in section A), the power, or the average proportion of true IBD segments reported (in section B), the accuracy of detected IBDs that share at least 50% overlap with true IBDs divided by the number of reported IBDs (in section C), and the length discrepancy of detected segments (in section D).

Section A of FIG. 12 shows the run time of different methods for 4,000 haplotypes with a chromosome length of 10 Mbps. In the experiments, across IBDs of all lengths, RaPID was much faster than GERMLINE, both of which are much faster than IBD seq. Of note, each of the benchmark runs of RaPID was completed in less than 2 s. RaPID was more than 100 times faster than GERMLINE for detecting IBDs with a target length of 3 cM. For detecting IBDs with a target length of 1.5 cM, RaPID was 25 times faster. The contrast of run time difference of RaPID and existing methods was even greater for larger samples. IBD detection tools that require pairwise comparison of all haplotypes are generally not scalable for a large number of haplotypes. As a result, they are very slow compared to GERMLINE and RaPID. While the run time for GERMLINE is linearly related to the sample size when the sequences are random, real genetic sequences are related and contain extensive shared segments. As a result, GERMLINE slows down with increased copies of the repeated sequences due to the burden of over-seeding, while RaPID embraces the patterns of sharing thanks to the efficient indexing of PBWT, and maintains a linear behavior.

The randomization strategy allows for precise control of desired performance. As shown in sections B and C of FIG. 12, RaPID exhibited a consistently high power in detecting IBD segments ranging from 1 to 5 cM compared to the existing methods while maintaining a comparable high accuracy. Detecting short IBDs (1-3 cM) is notoriously difficult because at shorter lengths, the number of identical-by-state (IBS) segments among unrelated individuals may overwhelm the signal from the real IBD segments. The accuracy here is defined as the percentage of reported segments where 50% of their length is covered by a true IBD segment. The accuracy of RaPID remains comparable to other tools with a stricter cutoff (75%) and a more relaxed cutoff (25%).

RaPID offers a principled way for parameter tuning for different sets. In a simulation study, the tolerance of misspecification of window size and target length parameters was investigated. For detecting 5 cM segments, RaPID with both window size and target length optimized for detecting 1.5 cM would severely lose power (0.2). On the other hand, for detecting 1.5 cM segments, RaPID with both window size and target length optimized for detecting 5 cM suffers low accuracy (0.5). Therefore, to maximize power and accuracy for any particular length range, RaPID with accurately determined parameters should be used.

The accurate inference of the length of an IBD segment is important for accurate population genetics modeling. RaPID also showed smaller length bias compared to IBDseq and GERMLINE, as shown in section D of FIG. 12. Notably, RaPID tended to overestimate the length by about 0.4 cM across all IBD lengths. This is understandable as PBWT reports any streak of windows with matching projections, and it is likely that windows for a true IBD segment be surrounded by several windows with matching projections by chance.

Figure 13:
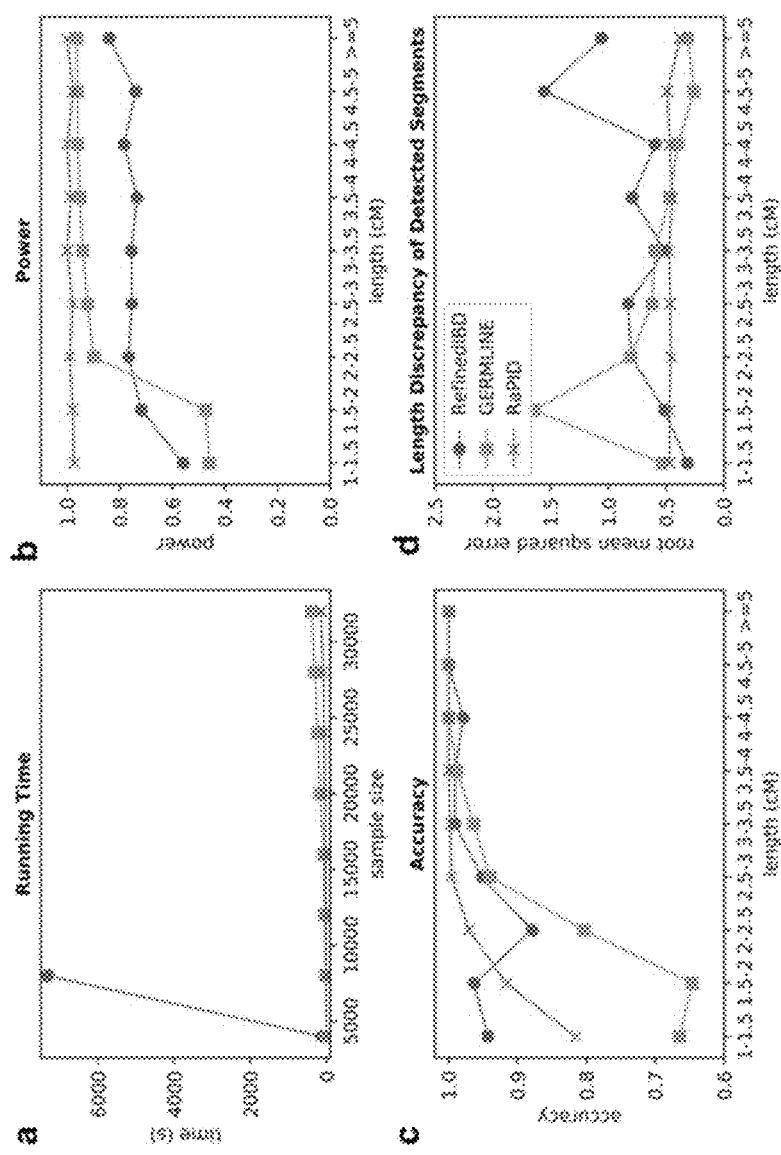
FIG. 13 graphically depicts benchmarking results of the RaPID method of FIG. 11, with simulated sequences with a chromosome length of 10 Mbps (million base pairs) thinned by choosing the variant site with the highest minor allele frequency in every 80 variant sites.

Performance of RaPID in sequencing data can be transferred to other genotype platforms with different marker density and error rates. To demonstrate this, thinned genotyping data was generated that resembled that of a typical genotyping platform by choosing the variant site with the highest minor allele frequency in every 80 consecutive variant sites from our simulated data. As shown in section B of FIG. 13, RaPID has consistently superior detection power over GERMLINE and RefinedIBD. The length discrepancy of RaPID across different target lengths remains constant in the thinned data (section D of FIG. 13). RefinedIBD has higher accuracy for shorter IBD segments (section C of FIG. 13) given its haplotype model, but it is significantly slower than RaPID (section A of FIG. 13). The accuracy of RaPID again remains comparable to other tools with a stricter overlap cutoff (75%) and more relaxed cutoff (25%). The accuracy of RefinedIBD with the stricter overlap cutoff remains higher, especially for shorter IBDs. It should be noted that RefinedIBD cannot tolerate genotyping error well. As a result, long IBD segments may be split into multiple short IBD segments. The short IBD segments were merged by allowing a 0.6 cM gap between every two IBD segments and at most two homozygous discordant genotypes, according to the recommendations from the author of RefinedIBD.

To demonstrate the run time and quality of IBD segment calls of RaPID, RaPID was applied to the genotypes of the UK Biobank participants. The X chromosomes of all 223,507 male participants were chosen to benchmark RaPID without the potential complications due to phasing inaccuracy. RaPID was also ran for chromosome 22 of all phased haplotypes of 487,409 participants. The detection of IBD segments with lengths ≥5 cM and ≥10 cM was limited. Notably, ≥5 cM is the range most informative for genetic genealogy. In expectation of complexity in real data, conservative parameter settings were used: (i) physical distance cutoff to cover 90% of target genetic length and (ii) estimated p that is greater than 90% of windows. While these settings reduce the running speed, the power and accuracy were expected to be high, even with imperfect phasing (one major switch error per 20 Mbps).

Figure 14:
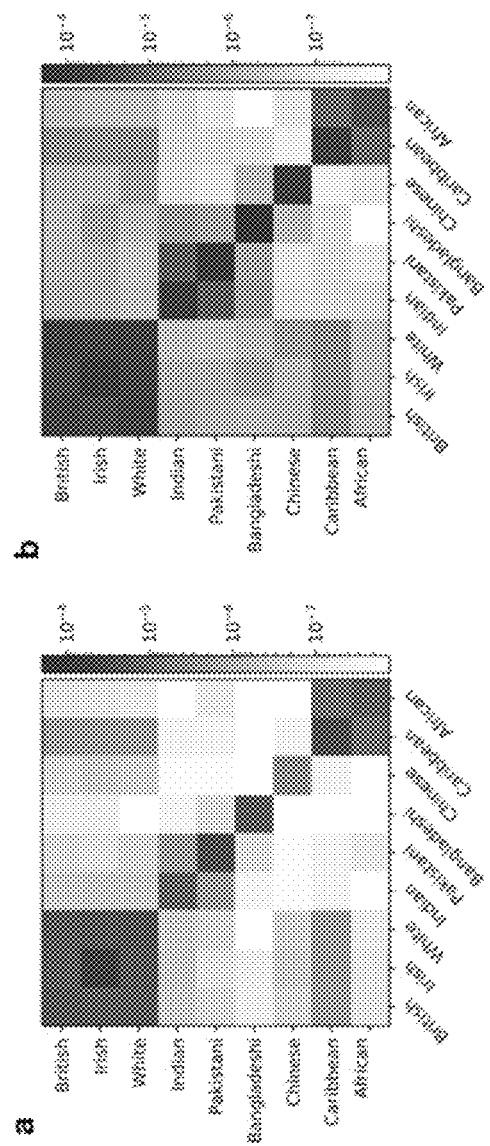
FIG. 14 graphically depicts the kinship values (in log scale) among different ethnic groups in the UK Biobank using detected IBD segments with a length of 5 cM and above in chromosome 22 (in section A) and chromosome X (in section B).

The average kinship was plotted based on the identified IBD segments among nine self-reported ethnic groups excluding individuals who reported multiple racial/ethnic groups (FIG. 14). The objective was to verify whether more IBD segments are detected within each group versus between different groups. As expected, IBDs within ethnic groups were stronger than that between ethnic groups. Also, IBDs within each racial group were stronger than that between racial groups. Moreover, the patterns were grossly consistent between chromosome 22 and chromosome X. Nonetheless, chromosome X showed stronger IBD signals, reflecting that chromosome X typically undergoes less meiotic recombinations than autosomes.

The IBD segments identified by RaPID were compared to the genetic relationships. Notably, up to third-degree relatedness, including MZ twins, parent-offspring, full siblings, second degree (half siblings and avuncular), and third degree (e.g., first cousins) were extracted from UK Biobank-distributed files, which was originally generated by the UK Biobank team using the KING program applied to genotypes over a filtered set of markers across the genome. Note that KING estimated the global average IBD at SNP level and did not estimate any IBD segments.

Figure 15:
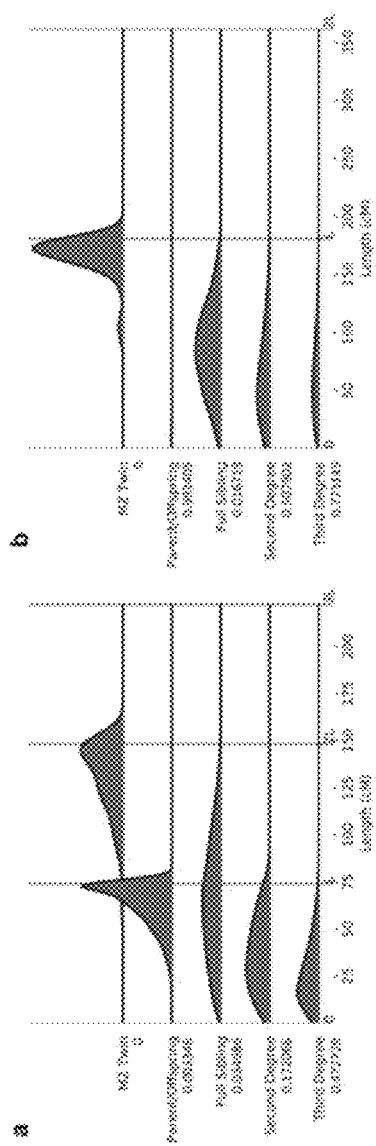
FIG. 15 graphically depicts the probability distributions of the sum of genetic lengths shared among pairs of individuals in five types of relatedness using detected IBD segments by RaPID with a target length of 5 cM and above in chromosome 22 for all participants (in section A) and chromosome X for male participants (in section B).

For all pairs of individuals within third-degree relatedness, the distribution of the total length of IBD segments was plotted among each pair stratified by their relationships (FIG. 15). The length distributions were largely consistent with expectations. Notably, for a significant proportion of pairs, no IBDs were observed.

Figure 16:
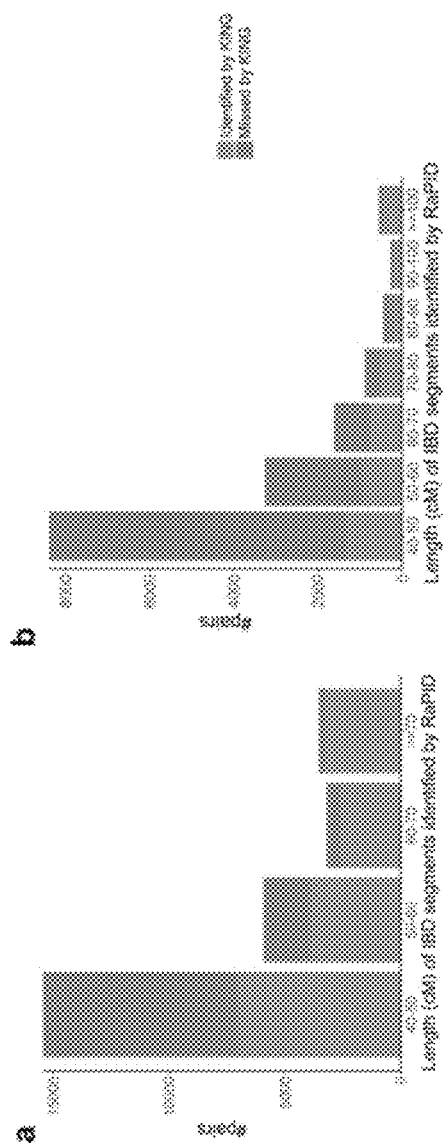
FIG. 16 graphically depicts the number of individual pairs with IBD segments identified by RaPID in chromosome 22 (in section A) and chromosome X (in section B), stratified by IBD length, and the number of such pairs that are also identified by KING.

RaPID identified a large number of pairs of individuals who share an IBD segment over 40 cM yet not included in the UK Biobank KING results. As shown in section B of FIG. 16, while KING identified 86% of the pairs in chromosome X with IBD length ≥100 cM identified by RaPID, KING missed 79 pairs with IBD segments ≥100 cM. It was verified that each of these segments demonstrated a much lower mismatch rate within the segments than outside of the segments. This paradox is possible because two individuals separated by more than three meiosis over the entire 196 cM X chromosome have a small but non-zero probability to have zero crossovers over the total 588 cM. Moreover, only 16% of the pairs with IBD length 40-50 cM in chromosome X were identified by RaPID while 46% of pairs with IBD length 40-50 cM in chromosome 22 had been reported by KING. This is similarly possible because most observed IBD segments with a length of 40-50 cM may be from distantly related pairs of individuals that are separated by >3 meiosis. Therefore, the results highlighted the expected discrepancies between the genealogical relationships and the realized sharing of IBD segments. Of note, chromosome 22 results between RaPID and KING are more consistent—only about 54% of the pairs sharing a 40-50 cM segments are not detected by KING. The main reason is probably that for the same length, IBDs in chromosome X indicate deeper genetic relationships than that in autosomes. In general, the results showed that IBD-based methods for genetic relationship inference would reveal more genetic relationships in biobank-scale datasets.

Dynamic PBWT

The PBWT algorithms discussed in detail above are based on arrays, which do not support dynamic updates. Accordingly, the entire PBWT must be rebuilt if new haplotypes are to be added, or existing haplotypes are to be deleted. As such, an embodiment of the system of FIG. 1 utilizes dynamic PBWT, or d-PBWT, to dynamically update the PBWT without the need to rebuild the entire system.

Like PBWT, the d-PBWT consists of N columns, each corresponds to one site. Column k is a doubly linked list of M nodes that represents the reverse prefix sorting of all M sequences at site k. Each column has a top node. The top node of column k is noted as (k, 0), containing the first sequence in reverse prefix sorting at column k. A node n in column k is noted as (k, i) if it takes i node traversals to reach n from the top node of column k. All necessary PBWT pointers can be encapsulated at (k, i), including $a_k[i]$, $d_k[i]$, $u_k[i]$, and $v_k[i]$ inside individual nodes; a node n has one function, w, and six properties. The properties are above, below, sequenceID, d, u, and v. The n.above property represents (k, i−1) and the n.below property represents (k, i+1). The n.sequenceID property is an integer $\in \{0 \ldots M-1\}$ that is unique to the sequence n represents (for example, n.sequenceID is $a_k[i]$). n[j, k] is equivalent to $y_k^i[j, k]$, and $X_{n.sequenceID}[j, k]$. n.d is equivalent to $d_k[i]$, (for example, n.d=$\min_{0 \leq j \leq k} s.t. n[j, k]=n.above[j, k]$). Each node also has u and v pointers that make up the extension function, which are equivalent to the u and v arrays as well. As such, they point to the node in the next column of the first sequence below them (self-included) that has 0 (for u) or 1 (for v). n.w(h) gets/sets n.u if h=0, otherwise the system sets n.v. Lastly, the haplotype panel of d-PBWT is a dynamic array of M haplotypes. The equivalencies between data structures of PBWT and d-PBWT are summarized in Table 1.

TABLE 1

| Entity | PBWT | d-PBWT |
| --- | --- | --- |
| Column k | $a_k$, $d_k$, $u_k$, $v_k$ | Linked list hung from top node at k |
| Index i at column k | $a_k[i]$, $d_k[i]$, $u_k[i]$, $v_k[i]$ | Node (n) that has i nodes above it and is in column k |
| Sequence name | $a_k[i]$ | n.sequenceID |
| Match length | $d_k[i]$ | n.d |
| Move to previous sequence in reverse prefix sorting | $a_k[i-1]$, $d_k[i-1]$, $u_k[i-1]$, $v_k[i-1]$ | n.above |
| Move to next sequence in reverse prefix sorting | $a_k[i+1]$, $d_k[i+1]$, $u_k[i+1]$, $v_k[i+1]$ | n.below |
| Move to next site by extension function | $u_k[i]$, $v_k[i]$, $u_k[i, h]$ | n.u, n.v, n.w(h) |
| Substring in original haplotype | $y_k[j, k)$, $x_{a_k[i]}[j, k)$ | n[j, k], $x_{n.sequenceID}[j, k)$ |

The insertion algorithm works by first inserting the nodes of z in the correct position in each column and then calculating the divergence values after. This is analogous to first updating the prefix arrays and then updating the divergence arrays. This is done by first sweeping forwards through the data to insert the nodes, and then sweeping backwards through the data to calculate the divergence values. z is inserted into the dynamic haplotype panel in the forward sweep.

Figure 17:
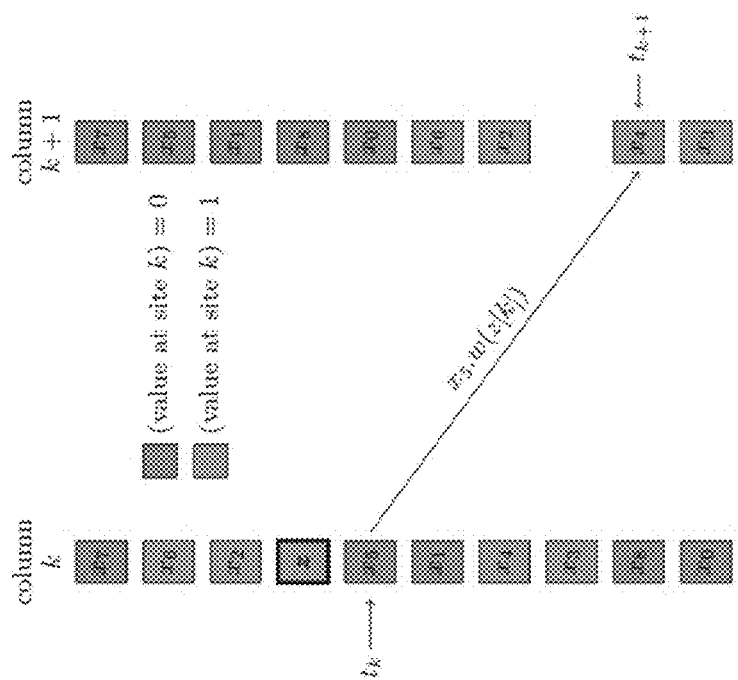
FIG. 17 shows an insertion update to the PBWT. The insertion location z=of z at the next column $t_k \cdot w(z[k])$ returns $t_{k+1}$, due to the first sequence below $x_5(t_k)$ having the same value as z at k is $x4 \cdot t_k \cdot w(z[k])$, pointing to the k+1 node of the first sequence below $t_k$ ($t_k$ inclusive) that has the same value as z at k. Therefore, $t_k \cdot w(z[k])$ points to the k+1 node of $x_4$.

As shown in FIG. 17, the prefix panel is updated by keeping track of the node that z should be above and then inserting z above said node. $t_k$ is defined as the node that z should be above in column k. If $t_k$ is known, $t_{k+1}$ can be calculated using the extension function. The sequence that is below z at column k+1 is the first sequence below z (not inclusive) that has the same value as z at k, i.e., $t_{k+1}=t_k \cdot w(z[k])$. This is also used to calculate all $t_k$'s and to insert z above them.

Figure 18:
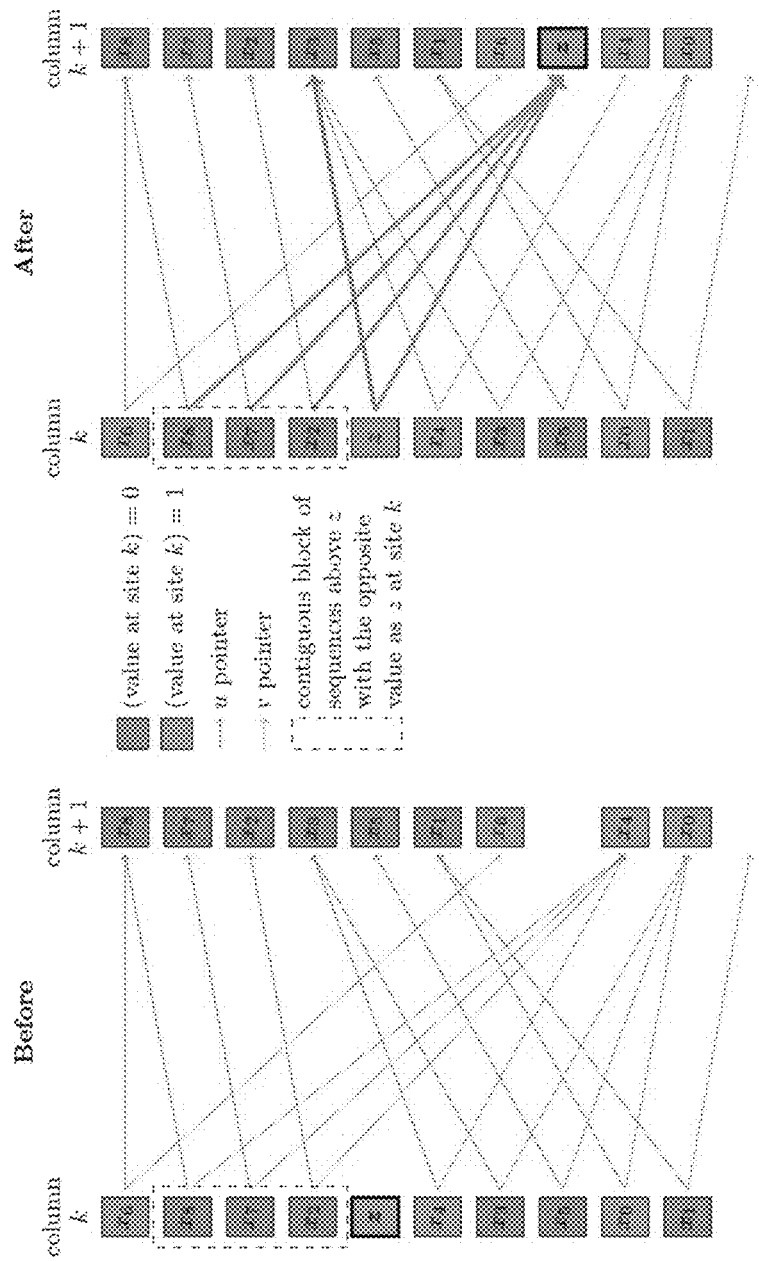
FIG. 18 shows the updating of u and v pointers when inserting the z node into column k+1. The updated items are bold, including z, four v pointers, and one u pointer.

The u and v pointers must be maintained. The contiguous group of sequences directly above z at k that have the opposite of z[k] at k must have their $$\begin{cases} u \text{ if } z[k] = 0 \\ v \text{ otherwise } (z[k] = 1) \end{cases}$$

pointer updated to point to $z_{k+1}$. Due to linkage disequilibrium (Naseri, Holzhauser, et al. 2019), this will be a small constant on average. Furthermore, $z_k \cdot w(z[k])$ is equal to $z_{k+1}$ and $z_k \cdot w(\text{opposite of } z[k])$ is equivalent to $t_k \cdot w(\text{opposite of } z[k])$ ($z_k$ is the node of z in column k). Therefore, u and v pointers of column k are updated after insertion of $z_{k+1}$ into column k+1, as shown in FIG. 18.

Figure 19:
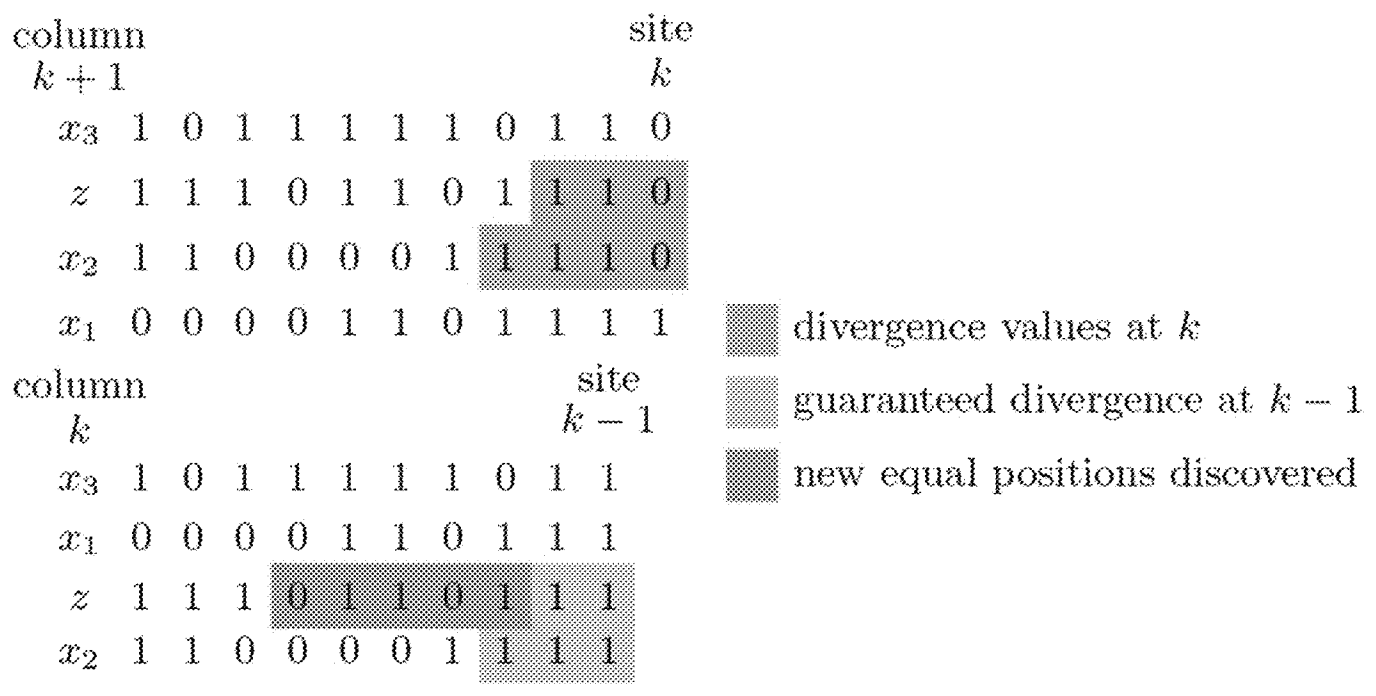

Finally, the divergence values are updated, as shown in FIG. 19. For each column k, only 2 divergence values need to be set, the divergence of z and the divergence of z.below; all other divergence values remain unchanged because the sequence above all other sequences remain unchanged. The divergence values are updated by going backwards through the columns and keeping track of the minimum divergence value (the longest match) found so far. A key observation is that at any column k, the divergence value of z must be at least the divergence value of z at k+1, i.e., $z_k \cdot d \leq z_{k+1} \cdot d$. This is true because if the sequence above z at k+1 matches with z r sites backwards from k+1, then that sequence will be above z at k and the sites will still match. The same applies for z and z·below. Therefore, to calculate the divergence values, the system scans from k=N→1 keeping track of divergence value of previous column. The divergence value of the $z_k$·below and $z_k$ is calculated by decrementing from divergence of $z_{k+1}$·below and $z_{k+1}$ until the first site that is different is found.

The time complexity of the Insertion algorithm is average case O(N). This is average case instead of worst case solely because of updating the u and v pointers and insertion of z into the dynamic haplotype panel. However, as stated, because of linkage disequilibrium, a case where the constant is non-negligible is extremely rare. Insertion of z into the dynamic haplotype panel is amortized O(N), therefore it is average case O(N). The insertion of the nodes of z into the correct position in each column is worst case O(N) because insertion into one column is constant time and there are N columns inserted into. The divergence calculation is also worst case O(N), because the outer loop runs for N iterations and the sum of all iterations of the inner loop will beat most N. The sum of all iterations of the inner loop will be at most N because it decrements an index from N→0 over the whole algorithm. The fact that a 'virtual insertion' algorithm (i.e., finding all divergence and $t_k$ values without updating u and v pointers or inserting z) is worst case O(N) will be used later to show the time complexity of the query algorithms.

The set maximal match query virtually inserts z into the d-PBWT. The sweep back of the insertion algorithm is modified so that set-maximal matches are simultaneously outputted. The set maximal match query is fairly straightforward after one vital element is understood. If z's locally maximal match ending at k matches further back than its locally maximal match ending at k+1, then z's locally maximal match ending at k is a set maximal match. Therefore, the system can compare divergence values at k and k+1 when calculating them to find and output set maximal matches.

A match is a set maximal if the match is locally maximal and there is no match with z that encompasses this match. It is known that the match is locally maximal because it is defined as 'locally maximal match ending at k' and it ends at k; therefore it is locally maximal (it is known that it ends at k because if it did not, the locally maximal matches of k and k+1 would match to the same point). Lastly, if there was a match with z that encompassed this match, then the locally maximal matches of k and k+1 would match to the same point. Therefore, the z's locally maximal match ending at k is a set-maximal match and can be outputted. Furthermore, there might be multiple sequences with this match, this is easily checked with divergence values.

Lastly, since the sequence above and below z cannot match z with the same divergence, locally maximal matches will either be all above or all below. Therefore, only the direction with the smaller divergence value (the longer match) will be checked. Assuming the sequence above and below z in the sort order match z with the same divergence, the sequence above has value 0 one position behind and the sequence below has value 1. z must have either 0 or 1 at this position. Therefore, the sequences above and below z do not match z with the same divergence.

The time complexity of the Set Maximal Match Query algorithm is worst case O(N+c). The virtual insertion is O(N) because the haplotype panel and the u and v pointers are not updated. The while loops are only entered when there is a set maximal match to output and each match is outputted exactly once. Therefore the sum of iterations of the output while loops is bounded by c (number of matches found) and the whole algorithm is O(N+c).

To find long matches without using LEAP arrays in d-PBWT in worst case O(N+c) time, the divergence values for the query algorithm must be calculated. First, z is virtually inserted into the data structure to obtain all $t_k$ values and all new divergence values if z was inserted. Then, a third sweep of the data is performed while keeping track of a matching block, without updating the haplotype panel or the u and v pointers.

The goal of the system is to keep track of the block of sequences that match with z length L or longer until k. The boundaries of the block are denoted as $f_k^L$ and $g_k^L$, where $f_k^L$ points to the first sequence of the block and $g_k^L$ points to the first sequence below $f_k^L$ that is not in the block. Given $f_k^L$ and $g_k^L$, it is desired to calculate $f_{k+1}^L$ and $g_{k+1}^L$. First, the extension function is used; $f_k^L \cdot w(z,[k])$ provides the position in the column k+1 of the first sequence after $f_k^L$ that has the same value as z at k, and likewise with $g_k^L \cdot w(z,[k])$. Therefore, $f_k^L \cdot w(z,[k])$ and $g_k^L \cdot w(z,[k])$ provide $f_{k+1}^{L+1}$ and $g_{k+1}^{L+1}$, which mark the boundaries of the block of sequences that match with z length L+1 or longer until k+1. The difference between $\{f_{k+1}^{L+1}, g_{k+1}^{L+1}\}$ and $\{k_{k+1}^{L}, g_{k+1}^{L}\}$ is only the sequences that match with z length L until k1. Accordingly, the divergence values can be intuitively used to check if a sequence on the boundary matches with z length L. If it does, the boundary is moved to include it in the block. After both boundaries reach a sequence that does not match with z length L until k+1, $f_{k+1}^L$ and $g_{k+1}^L$ are calculated.

Figure 20:
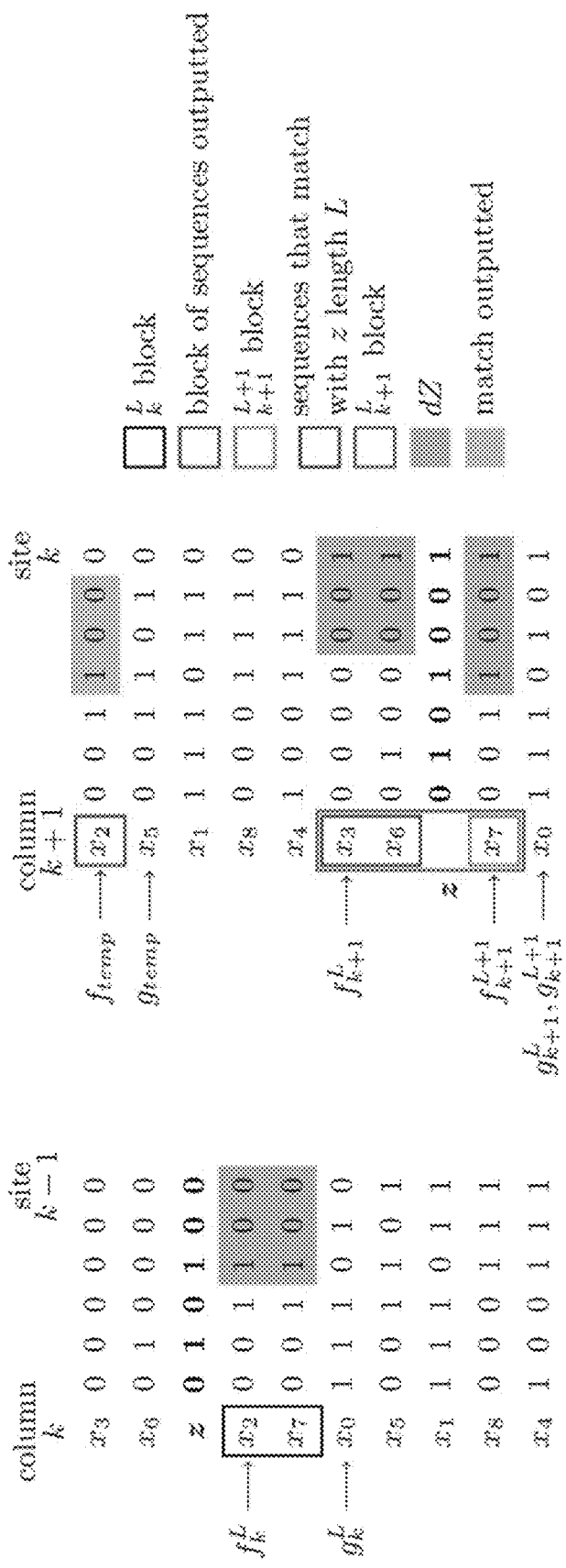
FIG. 20 shows the computation of $\{f_{k+1}^L, g_{k+1}^L\}$, using $\{f_k^L, g_k^L\}$ and extension function L=3. $f_k^L \cdot w(z[k])$ and $g_k^L \cdot w(z[k])$ provide $f_{k+1}^{L+1}$ and $g_{k+1}^{L+1}$. Next, the boundaries are expanded to include sequences that match with z length L until k+1. The new boundaries are $f_{k+1}^L$ and $g_{k+1}^L$. At the same time, $f_k^L \cdot w$(opposite of z[k]) and $g_k^L \cdot w$(opposite of z[k]) are used to obtain $f_{temp}$ and $g_{temp}$, which mark the block of sequences that match with z length L or longer and the match ends at site k.

It may be necessary to expand the $$L+1$$
$$k+1$$

block. For example, if the block is not empty ($f_{k+1}^{L+1} \neq g_{k+1}^{L+1}$), the divergence values of the sequences in the d-PBWT can be used to expand the boundaries. However, if the b lock is empty ($f_{k+1}^{L+1} = g_{k+1}^{L+1}$), the divergence values calculated during virtual insertion must be used to expand the boundaries initially. When the boundaries are expanded to include a new sequence in the block, the starting position of the match (k+1−L) must be stored in an array dZ to be outputted later. Meanwhile, $f_k^L \cdot w$(opposite of z[k]) and $g_k^L \cdot w$(opposite of z[k]) provide the block of sequences (in column k+1) that has matches length L or longer, until k and their match ends at k; these results are outputted, and the procedure is repeated for all k to output all matches longer than L between query sequence and database, as shown in FIG. 20.

The Long Match Query algorithm runs in worst case O(N+c) time. The virtual insertion portion of the algorithm runs in worst case O(N) because the haplotype panel and the u and v pointers are not updated. The query sweep loop has N iterations. All operations in one iteration of the query sweep loop take constant time except for the output while loop and the boundary expansion while loop. The output while loop will only output each match once, therefore the sum of all times it is entered in the algorithm is c, the number of matches found. The boundary expansion loop is entered once for every match that has length L (exactly) at some k. Every match will have length L exactly one time throughout the whole iteration of the algorithm, therefore the sum of all times the boundary expansion loop is entered is c. Therefore the algorithm runs in worst case O(N+c) time.

Deletion of a sequence from the d-PBWT occurs as follows. If sequence i is to be deleted, sequence $x_{M-1}$ needs to have the sequenceID of all its nodes changed from M−1 to i, so that the sequenceID definition is maintained after deletion of $x_i$. Furthermore, an array of pointers to the node in column 0 of each node needs to be kept so that the node of xi in column 0 can be accessed in constant time (Maintenance of this array is just an amortized constant time operation in the insertion and deletion algorithms). The contiguous block of sequences above the node of $x_i$ in column k needs to have their {u if $x_i$[k]=1, v otherwise} pointers updated. The pointers are set to the value of the node below $x_i$'s node. Lastly, the node of $x_i$ in each column is deleted and the divergence of the node below it is updated. The whole algorithm can be done in one sweep. The time complexity of this algorithm is average case O(N). This is not worst case because of the update of the u and v pointers and haplotype panel. However, as stated above, the update of the dynamic haplotype panel is amortized O(N) and the number of u and v pointers that will be updated per column will be a small constant on average.

Equivalencies between data structures of PBWT and d-PBWT (as shown in Table 1 above) suggest that all construction algorithms and search algorithms can be translated between PBWT and d-PBWT with minimal changes. Moreover, the d-PBWT data structure can be initialized by direct bulk conversion from an existing PBWT. Conversion of the d-PBWT to a PBWT in O(MN) time is trivial given its description, as is conversion of a PBWT to a d-PBWT. While the fact that a Long Match Query algorithm that runs in worst case O(N) is an interesting theoretical development, an average case O(N) algorithm that only sweeps through the data once may be more useful for real world applications, particularly implementations that use memory mapping.

Conclusion

The d-PBWT methods discussed above enable efficient genealogical search in large databases. For example, large consumer-facing population databases hosting millions of individuals' haplotypes typically have a constant burden of maintaining the population haplotype data structure in order to serve to report real-time genealogical search results. Dynamic PBWT provides a practical solution for maintaining the population haplotype data structure. The insertion and deletion algorithms can be implemented to handle high-volume updates in a real-time fashion. Meanwhile, the performance of genealogical search queries can be guaranteed by efficient long match query algorithms.

All of the long match algorithms discussed above, including the L-PBWT-query and d-PBWT, achieve average case time complexity independent to database size. The differences between the L-PBWT-query and d-PBWT are their worst-case time complexity, the number of sweeps required, and the memory needed for holding the additional auxiliary data structures. While in practice the optimal algorithm of choice may be a tradeoff of these and other factors, a reasonable balance is provided by d-PBWT, as it only takes one sweep, with average linear time independent to panel size, and no additional memory for LEAP arrays.

Modifying RaPID for Direct Use of Genetic Distances in PBWT

RaPID was modified to allow direct use of genetic distances in PBWT. RaPID can take the minimum target length directly in cM and will return all detected segments greater than or equal to the given length without post-processing of data. The program holds a genetic mapping table for all the available sites and the PBWT has been modified to work directly with the genetic length instead of the number of sites.

Figure 21:
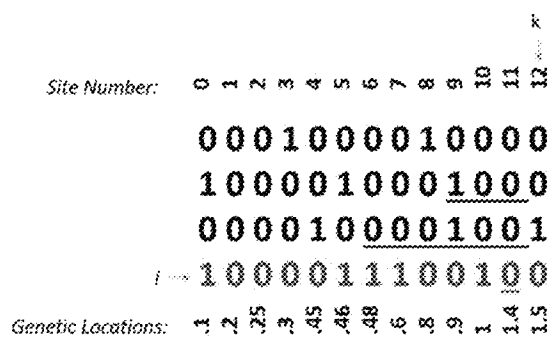

In some embodiments, a modification of PBWT can handle genetic lengths directly. The minimum length of a match can be provided in terms of genetic distance. The algorithm sorts the sequences by the reversed prefix order (as does PBWT). By sorting the sequences based on their prefix order, all blocks of matches are put in the same block. In this method, the divergence values (d[i]) are computed at each site with regard to the genetic distance. The array g contains the genetic location at each site. Divergence values for each sequence at each site contain the maximum index (site number) that the sequence matches with its immediately preceding neighbor in the prefix sorted order. The block of matches at each site (k) is then separated by a sequence where g[d[i]]>k−L. L is the minimum length in terms of the number of sites and k determines the site number. Assuming the length is given in terms of genetic distance (cM), then the block of matches is separated by a sequence with the condition g[d[i]]>g[k]−$L_g$, where $L_g$ is the minimum length in terms of genetic distance and g[k] is the genetic location at the site k. FIG. 21 shows a simple example of a panel in the reversed prefix order. The genetic locations are also provided for the sites at the bottom of the panel. As the panel at each site is sorted, we check for the condition: g[d[i]]>g[k]−$L_g$. If the condition is held, all the matches with alternating values will be reported.

Application

The methods described herein may be implemented on a computer readable medium. The computer readable may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program PIN embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program PIN embodied on a computer readable medium may be transmitted using any appropriate medium, including but not limited to wireless, wire-line, optical fiber cable, radio frequency, etc., or any suitable combination of the foregoing. Computer program PIN for carrying out operations for aspects of the present invention may be written in any combination of one or more programming languages, including an object oriented programming language such as Java, C#, C++ or the like and conventional procedural programming languages, such as the "C" programming language or similar programming languages.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

REFERENCES

Belbin G M, Odgis J, Sorokin E P, Yee M C, Kohli S, Glicksberg B S, Gignoux C R, Wojcik G L, Van Vleck T, Jeff J M, et al. Genetic identification of a common collagen disease in Puerto Ricans via identity-by-descent mapping in a health system. Elife. 2017; 6: e62500.

Bercovici S, Meek C, Wexler Y, Geiger D. Estimating genome-wide IBD sharing from SNP data via an efficient hidden Markov model of LD with application to gene mapping. Bioinformatics. 2010; 26: i175-82.

Browning B. L., Browning S. R. (2011) A fast, powerful method for detecting identity by descent. Am. J. Hum. Genet., 88, 173-182.

Browning B. L., Browning S. R. (2013a) Detecting identity by descent and estimating genotype error rates in sequence data. Am. J. Hum. Genet., 93, 840-851.

Browning B. L., Browning S. R. (2013b) Improving the accuracy and efficiency of identity-by-descent detection in population data. Genetics, 194, 459-471.

Browning S R, Thompson E A. Detecting rare variant associations by identity-by-descent mapping in case-control studies. Genetics. 2012; 190:1521-31.

Burrows, M., Wheeler, D. J.: A block-sorting lossless data compression algorithm. Digital Equipment Corporation, Tech. Rep. 124. (1994).

Bycroft C, Freeman C, Petkova D, Band G, Elliott L T, Sharp K, Motyer A, Vukcevic D, Delaneau O, O'Connell J, et al. The UK Biobank resource with deep phenotyping and genomic data. Nature. 2018; 562:203-9.

Campbell N. R. et al. (2015) Genotyping-in-Thousands by sequencing (GT-seq): a cost effective SNP genotyping method based on custom amplicon sequencing. Mol. Ecol. Resour., 15, 855-867.

Ceballos F C, Joshi P K, Clark D W, Ramsay M, Wilson J F. Runs of homozygosity: windows into population history and trait architecture. Nat Rev Genet. 2018; 19:220-34.

Chen G K, Marjoram P, Wall J D. Fast and flexible simulation of DNA sequence data. Genome Res. 2009; 19:136-42.

Durbin R. Efficient haplotype matching and storage using the positional Burrows-Wheeler transform (PBWT). Bioinformatics. 2014; 30:1266-72.

Erlich Y. et al. (2018) Identity inference of genomic data using long-range familial searches. Science, 362, 690-694.

Garrison, E., Siren, J., Novak, A., Hickey, G., Eizenga, J., Dawson, E., Jones, W., Garg, S., Markello, C., Lin, M., et al: Variation graph toolkit improves read mapping by representing genetic variation in the reference. Nature Biotechnology 36 (9), 875 (2018).

Gusev A, Lowe J K, Stoffel M, Daly M J, Altshuler D, Breslow J L, Friedman J M, Pe'er I. Whole population, genome-wide mapping of hidden relatedness. Genome Res. 2009; 19:318-26.

Han E, Carbonetto P, Curtis R E, Wang Y, Granka J M, Byrnes J, Noto K, Kermany A R, Myres N M, Barber M J, et al. Clustering of 770,000 genomes reveals post-colonial population structure of North America. Nat Commun. 2017; 8:14238.

Henn B M, Hon L, Macpherson J M, Eriksson N, Saxonov S, Pe'er I, Mountain J L. Cryptic distant relatives are common in both isolated and cosmopolitan genetic samples. PLoS One. 2012; 7: e34267.

Homburger J R, Moreno-Estrada A, Gignoux C R, Nelson D, Sanchez E, Ortiz-Tello P, Pons-Estel B A, Acevedo-Vasquez E, Miranda P, Langefeld C D, et al. Genomic insights into the ancestry and demographic history of South America. PLoS Genet. 2015; 11: e1005602.

Jiang Z. et al. (2016) Genome wide sampling sequencing for SNP genotyping: methods, challenges and future development. Int. J. Biol. Sci., 12, 100-108.

Khan R., Mittelman D. (2018) Consumer genomics will change your life, whether you get tested or not. Genome Biol., 19, 120.

Loh P. R. et al. (2016a) Fast and accurate long-range phasing in a UK Biobank cohort. Nat. Genet., 48, 811-816.

Loh P. R. et al. (2016b) Reference-based phasing using the Haplotype Reference Consortium panel. Nat. Genet., 48, 1443-1448.

Manichaikul A, Mychaleckyj J C, Rich S S, Daly K, Sale M, Chen W M. Robust relationship inference in genome-wide association studies. Bioinformatics. 2010; 26:2867-73.

Nakatsuka N, Moorjani P, Rai N, Sarkar B, Tandon A, Patterson N, Bhavani G S, Girisha K M, Mustak M S, Srinivasan S, et al. The promise of discovering population-specific disease-associated genes in South Asia. Nat Genet. 2017; 49:1403-7.

Naseri A, Liu X, Zhang S, Zhi D. (2019, Jul. 2). Random projection-based IBD detection (RaPID) (version src 1.2.3). Zenodo. https://doi.org/10.5281/zenodo.3266342.

Naseri A. et al. (2017). Ultra-fast identity by descent detection in biobank-scale cohorts using positional Burrows-Wheeler transform. bioRxiv, 103325.

Naseri, A., Holzhauser, E., Zhi, D., Zhang, S.: Efficient haplotype matching between a query and a panel for genealogical search. Bioinformatics 35(14), i233-i241 (2019).

Naseri, A., Liu, X., Tang, K., Zhang, S., Zhi, D.: RaPID: ultra-fast, powerful, and accurate detection of segments identical by descent (IBD) in biobank-scale cohorts. Genome Biology 20(1), 143 (2019).

Purcell S. et al. (2007) PLINK: a tool set for whole-genome association and population-based linkage analyses. Am. J. Hum. Genet., 81, 559-575.

Ralph P, Coop G. The geography of recent genetic ancestry across Europe. PLoS Biol. 2013; 11: e1001555.

Rodriguez J. M. et al. (2013). An accurate method for inferring relatedness in large datasets of unphased genotypes via an embedded likelihood-ratio test. In: Proceedings of the 17th International Conference on Research in Computational Molecular Biology, pp. 212-229. Springer, Berlin, Heidelberg.

Rodriguez J. M. et al. (2015) Parente2: a fast and accurate method for detecting identity by descent. Genome Res., 25, 280-289.

Sanaullah A, Zhi D, Zhang S. d-PBWT: dynamic positional Burrows-Wheeler transform. bioRxiv. 2020; 2020.01.14.906487.

Shchur V, Nielsen R. On the number of siblings and p-th cousins in a large population sample. J Math Biol. 2018; 77:1279-98.

Speed D, Balding D J. Relatedness in the post-genomic era: is it still useful? Nat Rev Genet. 2015; 16:33-44.

Sudlow C. et al. (2015) UK Biobank: an open access resource for identifying the causes of a wide range of complex diseases of middle and old age. PLoS Med., 12, e1001779.

Thompson E. A. (2013) Identity by descent: variation in meiosis, across genomes, and in populations. Genetics, 194, 301-326.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A genealogical indexing system comprising:
    a processor;
    a haplotype panel pool in electronic communication with a non-transitory computer-readable medium that is operably coupled to the processor, the haplotype panel pool including a plurality of panels that is indexed by a positional Burrows-Wheeler transform (PBWT) representation, each of the plurality of panels including a plurality of haplotypes, the haplotype panel pool having a set of variant sites, wherein each of the plurality of haplotypes is indexed by the PBWT representation in a reversed prefix order; and
    the non-transitory computer-readable medium having computer-readable instructions stored thereon that, when executed by the processor, cause the genealogical indexing system to automatically identify a genealogical match with an input genetic sequence by executing instructions comprising:
        selecting, via a computing nodule in electronic communication with the haplotype panel pool, a minimum identity-by-descent segment length value of at least one million base pairs, such that haplotype matches greater than or equal to the minimum identity-by-descent segment length indicate a match between the input genetic sequence and the haplotype panel pool, and such that haplotype matches lesser than the minimum identity-by-descent segment length indicate a lack of a match between the input genetic sequence and the haplotype panel pool;
        selecting, via the computing nodule in electronic communication with the haplotype panel pool, a plurality of portions of each of the plurality of panels to sample each of the plurality of panels;
        projecting, via the computing nodule in electronic communication with the haplotype panel pool, the sample to the set of variant sites for each of the plurality of panels in the haplotype panel pool, such that the sample can be compared against the samples in the haplotype panel pool via the set of variants;
        receiving, via the computing nodule in electronic communication with the haplotype panel pool, the input genetic sequence;
        automatically indexing, via a haplotype querying engine of the computing nodule in electronic communication with the haplotype panel pool, executable by the processor, the input genetic sequence by the PBWT representation, thereby transforming the input genetic sequence into a PBWT indexed input genetic sequence including the reversed prefix order;
        activating, via the haplotype querying engine of the computing nodule in electronic communication with the haplotype panel pool, an amount of the plurality of panels from the haplotype panel pool for testing;
        comparing, via the haplotype querying engine of the computing nodule in electronic communication with the haplotype panel pool, the PBWT indexed input genetic sequence with the amount of the plurality of panels by comparing the PBWT indexed input genetic sequence with the set of variant sites; and
        via the haplotype querying engine of the computing nodule in electronic communication with the haplotype panel pool, automatically identifying, in real-time and independent of a total number of haplotypes in the plurality of haplotypes, the genealogical match between the input genetic sequence and the haplotype pool by:
            based on a determination that the PBWT indexed input genetic sequence matches the amount of the plurality of panels by a value greater than or equal to the minimum identity-by-descent segment length of at least one million base pairs, determining the genealogical match between the input genetic sequence and the haplotype panel pool; and
            based on a determination that the PBWT indexed input genetic sequence does not match the amount of the plurality of panels by a value greater than or equal to the minimum identity-by-descent segment length of at least one million base pairs, determining a lack of the genealogical match between the input genetic sequence and the haplotype panel pool.

2. The genealogical indexing system of claim 1, wherein the instructions of automatically identifying the genealogical match between the input genetic sequence and the haplotype panel pool further comprise utilizing a long match query algorithm to compare the PBWT indexed input genetic sequence with the amount of the plurality of panels and determine if the PBWT indexed input genetic sequence matches the amount of the plurality of panels by a value greater than or equal to the minimum identity-by-descent segment length of at least one million base pairs.

3. The genealogical indexing system of claim 1, wherein the instructions further comprise, after projecting the sample to the set of variant sites for each of the plurality of panels in the haplotype panel pool, weighing, via the computing nodule in electronic communication with the haplotype panel pool, the set of variant sites to emphasize minor allele frequencies.

4. The genealogical indexing system of claim 1, wherein the PBWT representation is a dynamic representation providing for updating the haplotype panel pool.

5. The genealogical indexing system of claim 4, wherein the instructions further comprise dynamically updating, in real-time, via a haplotype ingestion engine of the computing nodule in electronic communication with the haplotype panel pool, executable by the processor, the haplotype panel pool.

6. The genealogical indexing system of claim 5, wherein the instructions further comprise adding, via the haplotype ingestion engine of the computing nodule in electronic communication with the haplotype panel pool, a new haplotype into the haplotype panel pool by:
indexing the new haplotype by the PBWT representation, thereby transforming the new haplotype into a PBWT indexed new haplotype including the reversed prefix order; and
inserting the PBWT indexed new haplotype into at least one of the plurality of panels.

7. The genealogical indexing system of claim 6, wherein the instructions further comprise adding the PBWT indexed new haplotype into at least one of the plurality of panels by inserting the PBWT indexed new haplotype into a correct position at each variant site of the set of variants and calculating divergence values at positions forward from the inserted PBWT indexed new haplotype.

8. The genealogical indexing system of claim 6, wherein the PBWT indexed new haplotype is from the input genetic sequence.

9. The genealogical indexing system of claim 5, wherein the instructions further comprise adding, via the haplotype ingestion engine of the computing nodule in electronic communication with the haplotype panel pool, a new haplotype into each of the plurality of panels by:
indexing the new haplotype by the PBWT representation, thereby transforming the new haplotype into a PBWT indexed new haplotype including the reversed prefix order; and
inserting the PBWT indexed new haplotype into a correct position at each variant site of the set of variants and calculating divergence values at positions forward from the inserted PBWT indexed new haplotype.

10. The genealogical indexing system of claim 4, wherein the instructions further comprise deleting, via a haplotype ingestion engine of the computing nodule in electronic communication with the haplotype panel pool, executable by the processor, a haplotype from the haplotype panel pool by removing the haplotype from at least one of the plurality of panels.

11. The genealogical indexing system of claim 1, wherein the instructions further comprise retrieving, via the computing nodule in electronic communication with the haplotype panel pool, a pre-computed genealogical match between the haplotype panel pool and the PBWT indexed input genetic sequence after the step of automatically indexing the input genetic sequence by the PBWT representation, such that the pre-computed genealogical match is displayed before the step of comparing the PBWT indexed input genetic sequence with the amount of the plurality of panels to find a match of the minimum identity-by-descent segment length of at least one million base pairs.

12. The genealogical indexing system of claim 1, wherein the instructions of determining the minimum identity-by-descent segment length value of at least one million base pairs further comprise determining, via the computing nodule in electronic communication with the haplotype panel pool, at least one of a physical distance and a genetic distance between divergence value updates of a long match query algorithm.

13. A genealogical indexing system comprising:
a processor;
a haplotype panel pool in electronic communication with a non-transitory computer-readable medium that is operably coupled to the processor; and
the non-transitory computer-readable medium having computer-readable instructions stored thereon that, when executed by the processor, cause the genealogical indexing system to automatically identify a genealogical match with an input genetic sequence by executing instructions comprising:
indexing the haplotype panel pool including a plurality of panels that via a dynamic positional Burrows-Wheeler transform (PBWT) representation, each of the plurality of panels including a plurality of haplotypes, the haplotype panel pool having a set of variant sites, wherein each of the plurality of haplotypes is indexed by the dynamic PBWT representation in a reversed prefix order;
selecting, via a computing nodule in electronic communication with the haplotype panel pool, a minimum identity-by-descent segment length value of at least one million base pairs, such that haplotype matches greater than or equal to the minimum identity-by-descent segment length indicate a match between the input genetic sequence and the haplotype panel pool, and such that haplotype matches lesser than the minimum identity-by-descent segment length indicate a lack of a match between the input genetic sequence and the haplotype panel pool;
selecting, via a computing nodule in electronic communication with the haplotype panel pool, a plurality of portions of each of the plurality of panels to sample each of the plurality of panels;
projecting, via a computing nodule in electronic communication with the haplotype panel pool, the sample to the set of variant sites for each of the plurality of panels in the haplotype panel pool, such that the sample can be compared against the samples in the haplotype panel pool via the set of variants;
after projecting the sample to the set of variant sites for each of the plurality of panels in the haplotype panel pool, weighing, via a computing nodule in electronic communication with the haplotype panel pool, the set of variant sites to emphasize minor allele frequencies;
receiving, via a computing nodule in electronic communication with the haplotype panel pool, the input genetic sequence;
automatically indexing, via a haplotype querying engine via a computing nodule in electronic communication with the haplotype panel pool, executable by the processor, the input genetic sequence by the dynamic PBWT representation, thereby transforming the input genetic sequence into a PBWT indexed input genetic sequence including the reversed prefix order;

activating, via the haplotype querying engine of the computing nodule in electronic communication with the haplotype panel pool, an amount of the plurality of panels from the haplotype panel pool for testing;

comparing, via the haplotype querying engine of the computing nodule in electronic communication with the haplotype panel pool, the PBWT indexed input genetic sequence with the amount of the plurality of panels by comparing the PBWT indexed input genetic sequence with the set of variant sites; and via the haplotype querying engine of the computing nodule in electronic communication with the haplotype panel pool, automatically identifying, in real-time and independent of a total number of haplotypes in the plurality of haplotypes, the genealogical match between the input genetic sequence and the haplotype pool by:

based on a determination that the PBWT indexed input genetic sequence matches the amount of the plurality of panels by a value greater than or equal to the minimum identity-by-descent segment length of at least one million base pairs, determining the genealogical match between the input genetic sequence and the haplotype panel pool; and based on a determination that the PBWT indexed input genetic sequence does not match the amount of the plurality of panels by a value greater than or equal to the minimum identity-by-descent segment length of at least one million base pairs, determining a lack of the genealogical match between the input genetic sequence and the haplotype panel pool.

14. The genealogical indexing system of claim 13, wherein the instructions of determining the genealogical match between the input genetic sequence and the haplotype panel pool further comprise utilizing a long match query algorithm to compare the PBWT indexed input genetic sequence with the amount of the plurality of panels and determine if the PBWT indexed input genetic sequence matches the amount of the plurality of panels by a value greater than or equal to the minimum identity-by-descent segment length of at least one million base pairs.

15. The genealogical indexing system of claim 13, wherein the instructions further comprise adding, via a haplotype ingestion engine of the computing nodule in electronic communication with the haplotype panel pool, executable by the processor, a new haplotype into the haplotype panel pool by:

indexing the new haplotype by the dynamic PBWT representation, thereby transforming the new haplotype into a PBWT indexed new haplotype including the reversed prefix order; and inserting the PBWT indexed new haplotype into at least one of the plurality of panels.

16. The genealogical indexing system of claim 15, wherein the instructions further comprise adding the PBWT indexed new haplotype into at least one of the plurality of panels by inserting the PBWT indexed new haplotype into a correct position at each variant site of the set of variants and calculating divergence values at positions forward from the inserted PBWT indexed new haplotype.

17. The genealogical indexing system of claim 13, wherein the instructions further comprise deleting, via a haplotype ingestion engine of the computing nodule in electronic communication with the haplotype panel pool, executable by the processor, a haplotype from the haplotype panel pool by removing the haplotype from at least one of the plurality of panels.

18. The genealogical indexing system of claim 13, wherein the instructions of determining the minimum identity-by-descent segment length value of at least one million base pairs further comprise determining, via the computing nodule in electronic communication with the haplotype panel pool, at least one of a physical distance and a genetic distance between divergence value updates of a long match query algorithm.

19. A genealogical indexing system comprising:

a processor;

a haplotype panel pool in electronic communication with a non-transitory computer-readable medium that is operably coupled to the processor, the haplotype panel pool including a plurality of panels that are indexed by a dynamic positional Burrows-Wheeler transform (PBWT) representation, each of the plurality of panels including a plurality of haplotypes, the haplotype panel pool having a set of variant sites; and the non-transitory computer-readable medium having computer-readable instructions stored thereon that, when executed by the processor, cause the genealogical indexing system to automatically identify a genealogical match with an input genetic sequence by executing instructions comprising:

indexing each of the plurality of haplotypes of the haplotype panel pool in a reversed prefix order via the dynamic PBWT representation;

selecting, via a computing nodule in electronic communication with the haplotype panel pool, a minimum identity-by-descent segment length value of at least one million base pairs, such that haplotype matches greater than or equal to the minimum identity-by-descent segment length indicate a match between the input genetic sequence and the haplotype panel pool, and such that haplotype matches lesser than the minimum identity-by-descent segment length indicate a lack of a match between the input genetic sequence and the haplotype panel pool;

selecting, via the computing nodule in electronic communication with the haplotype panel pool, a plurality of portions of each of the plurality of panels to sample each of the plurality of panels;

projecting, via the computing nodule in electronic communication with the haplotype panel pool, the sample to the set of variant sites for each of the plurality of panels in the haplotype panel pool, such that the sample can be compared against the samples in the haplotype panel pool via the set of variants;

after projecting the sample to the set of variant sites for each of the plurality of panels in the haplotype panel pool, weighing, via the computing nodule in electronic communication with the haplotype panel pool, the set of variant sites to emphasize minor allele frequencies;

receiving, via the computing nodule in electronic communication with the haplotype panel pool, the input genetic sequence;

automatically indexing, via a haplotype querying engine of the computing nodule in electronic communication with the haplotype panel pool, executable by the processor, the input genetic sequence by the dynamic PBWT representation, thereby transforming the input genetic sequence into a PBWT indexed input genetic sequence including the reversed prefix order;

activating, via the haplotype querying engine of the computing nodule in electronic communication with the haplotype panel pool, an amount of the plurality of panels from the haplotype panel pool for testing; and utilizing a long match query algorithm, comparing, via the haplotype querying engine of the computing nodule in electronic communication with the haplotype panel pool, the PBWT indexed input genetic sequence with the amount of the plurality of panels by comparing the PBWT indexed input genetic sequence with the set of variant sites, to automatically identify, in real-time and independent of a total number of haplotypes in the plurality of haplotypes, the genealogical match between the input genetic sequence and the haplotype pool by:

based on a determination that the PBWT indexed input genetic sequence matches the amount of the plurality of panels by the value greater than or equal to the minimum identity-by-descent segment length of at least one million base pairs, determining the genealogical match between the input genetic sequence and the haplotype panel pool; and based on a determination that the PBWT indexed input genetic sequence does not match the amount of the plurality of panels by a value greater than or equal to the minimum identity-by-descent segment length of at least one million base pairs, determining a lack of the genealogical match between the input genetic sequence and the haplotype panel pool.

* * * * *